United States Patent [19]

Brundish et al.

[11] Patent Number: 5,686,564
[45] Date of Patent: Nov. 11, 1997

[54] PEPTIDE DERIVATIVES CORRESPONDING TO THE CARBOXY TERMINAL SEQUENCE OF HIRUDIN

[75] Inventors: Derek Edward Brundish, Horsham, England; Hans Rink, Riehen, Switzerland; Markus Grütter, Hochwald, Switzerland; John Peter Priestle, Bubendorf, Switzerland; Albert Schmitz, Basel, Switzerland

[73] Assignee: Novartis Corporation, Summit, N.J.

[21] Appl. No.: 325,253

[22] PCT Filed: Apr. 15, 1993

[86] PCT No.: PCT/EP93/00908

§ 371 Date: Oct. 20, 1994

§ 102(e) Date: Oct. 20, 1994

[87] PCT Pub. No.: WO93/22344

PCT Pub. Date: Nov. 11, 1993

[30] Foreign Application Priority Data

Apr. 25, 1992 [GB] United Kingdom ............ 9209032

[51] Int. Cl.$^6$ ............... C07K 7/06; C12Q 1/56
[52] U.S. Cl. ............... 530/327; 530/328; 530/332; 530/345; 435/13; 435/214
[58] Field of Search ............... 530/350, 324, 530/330, 331, 329, 345, 325, 326, 327, 328, 332; 435/13, 214

[56] References Cited

U.S. PATENT DOCUMENTS

| | | | |
|---|---|---|---|
| 4,117,127 | 9/1978 | Okamoto et al. | 424/247 |
| 4,258,192 | 3/1981 | Okamoto et al. | 546/166 |
| 5,087,613 | 2/1992 | Courtney et al. | 530/324 |
| 5,112,615 | 5/1992 | Ito et al. | 530/300 |
| 5,118,790 | 6/1992 | Winant et al. | 530/324 |

FOREIGN PATENT DOCUMENTS

| | | |
|---|---|---|
| 0008746 | 3/1980 | European Pat. Off. . |
| 0372670 | 6/1990 | European Pat. Off. . |
| 2801478 | 7/1978 | Germany . |
| WO91/02750 | 3/1991 | WIPO . |

OTHER PUBLICATIONS

Nishikawa, S., et al., "Efficient Cleavage by α–thrombin of a Recombinant Fused Protein which Contains Insulin–like Growth Factor I", *Protein Engineering*, 1(6):487–492 (1987).

Remaut, E., et al., "Improved Plasmid Vectors with a Thermoinducible Expression and Temperature–Regulated Runaway Replication", *Gene*, 22:103–113 (1983).

Rink, H., et al., "A Large Fragment Approach to DNA Synthesis: Total Synthesis of a Gene for the Protease Inhibitor Eglin c from the Leech *Hirudo medicinalis* and Its Expression in *E. coli*", *Nucleic Acids Research*, 12:6369–6387 (1984).

Scharf, M., et al., "Primary Structures of New 'Iso–hirudins'", *FEBS*, 255(1):105–110 (1989).

Von Wilcken–Bergmann, B., et al., "A Synthetic Operon Containing 14 Bovine Pancreatic Trypsin Inhibitor Genes is Expressed in *E. coli*", *The EMBO Journal*, 5(12):3219–3225 (1986).

Yue, S–Y., et al., "Characterization of the Interactions of a Bifunctional Inhibitor with α–thrombin by Molecular Modeling and Peptide Synthesis", *Protein Engineering*, 5(1):77–85 (1992).

Altman, J.D., et al., "Intracellular Expression of BPT1 Fusion Proteins and Single Column Cleavage/Affinity Purification by Chymotrypsin", *Protein Engineering*, 4(5):593–600 (1991).

Buell, G., et al., "Optimizing the Expression in *E. coli* of a Synthetic Gene Encoding Somatomedin–C (IGF–I)", *Nucleic Acids Research*, 13(6):1923–1938 (1985).

DiMaio, J., et al., "A New Class of Potent Thrombin Inhibitors that Incorporates a Scissile Pseudopeptide Bond", *FEBS*, 282(1):47–52 (1991).

Gardella, T.J., et al., "Expression of Human Parathyroid Hormone–(1–84) in *Escherichia coli* as a Factor X–cleavable Fusion Protein", *J. Biol. Chem.*, 265(26):15854–15859 (1990).

Hellebust, H., et al., "Different Approaches to Stabilize a Recombinant Fusion Protein", *Biotechnology*, 7:165–168 (1989).

Knorr, R., et al., "New Coupling Reagents in Peptide Chemistry", *Tetrahedron Letters*, 30(15):1927–1930 (1989).

Maraganore, J.M., et al., "Design and Characterization of Hirulogs: A Novel Class of Bivalent Peptide Inhibitors of Thrombin", *Biochemistry*, 29:7095–7101 (1990).

Knupp, "Effect of Thrombin Inhibitors on Thrombin–Induced Platelet Melgase & Aggregation", (1988) Caplus 1988:92261.

*Primary Examiner*—Ceclia J. Tsang
*Assistant Examiner*—Patrick R. Delaney
*Attorney, Agent, or Firm*—Marla J. Mathias; Gregory D. Ferraro

[57] ABSTRACT

Novel compounds of the formula I

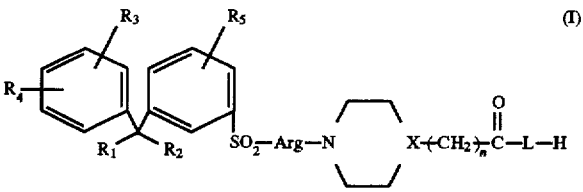

in which $R^1$ and $R^2$ are hydrogen, $C_1$–$C_4$ alkyl or are linked to form $C_3$–$C_7$ cycloalkyl and $R^3$, $R^4$ and $R^5$ are the same or different and are hydrogen, $C_1$–$C_4$ alkyl, hydroxy, $OR^6$, $SR^6$, halogen, $NR^7R^8$, $NO_2$, CN, $CONR^7R^8$ or $CO_2R^9$ wherein $R^6$ is $C_1$–$C_4$ alkyl or $C_7$–$C_{10}$ aralkyl and $R^7$, $R^8$ and $R^9$ are the same or different and are hydrogen, $C_1$–$C_4$ alkyl or $C_7$–$C_{10}$ aralkyl or $R^7$ and $R^8$ together with the nitrogen atom to which they are bound form 5 or 6 membered azacycloalkyl or oxazacycloalkyl; Arg is arginine [NH—CH($CH_2CH_2CH_2NH$—C(=NH)—$NH_2$)—CO]; X is methine CH or nitrogen; n is an integer from 0 to 7; L is a peptide linker, and H is the carboxy terminal end of hirudin, and salts thereof, are provided. The novel compounds are useful for the medical treatment or prevention of thrombosis or diseases caused by thrombosis or can be used for the determination of thrombin in blood as diagnostic reagents.

18 Claims, 1 Drawing Sheet

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: C-terminal ( v i ) ORIGINAL SOURCE:
        ( A ) ORGANISM: Hirudo medicinalis ( i x ) FEATURE:
        ( A ) NAME/KEY: Peptide
        ( B ) LOCATION: 1..11
        ( D ) OTHER INFORMATION: /note="amino acid 55-65 of desulpahtohirudin HV1 (EP 142860)"

( i x ) FEATURE:
        ( A ) NAME/KEY: Modified-site
        ( B ) LOCATION: 9
        ( D ) OTHER INFORMATION: /note="the Tyrosine may be esterified with sulphuric or phosphoric acid"

( x i ) SEQUENCE DESCRIPTION: SEQ ID NO: 1:

Asp Phe Glu Glu Ile Pro Glu Glu Tyr Leu Gln
1               5                   10

( 2 ) INFORMATION FOR SEQ ID NO: 2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: C-terminal ( v i ) ORIGINAL SOURCE:
     ( A ) ORGANISM: Hirudo medicinalis ( i x ) FEATURE:
     ( A ) NAME/KEY: Peptide
     ( B ) LOCATION: 1..12
     ( D ) OTHER INFORMATION: /note="amino acids 55-66 of
          desulphatohirudin HV3 (PA) (PCT 86/03493)"

( i x ) FEATURE:
     ( A ) NAME/KEY: Modified-site
     ( B ) LOCATION: 10
     ( D ) OTHER INFORMATION: /note="The tyrosine may be
          esterified with sulphuric or phosphoric acid"

( x i ) SEQUENCE DESCRIPTION: SEQ ID NO: 2:

Asp Phe Glu Pro Ile Pro Glu Asp Ala Tyr Asp Glu
1               5                   10

( 2 ) INFORMATION FOR SEQ ID NO: 3:

( i ) SEQUENCE CHARACTERISTICS:
          ( A ) LENGTH: 11 amino acids
          ( B ) TYPE: amino acid
          ( C ) STRANDEDNESS: single
          ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: C-terminal ( v i ) ORIGINAL SOURCE:
          ( A ) ORGANISM: Hirudo medicinalis ( i x ) FEATURE:
          ( A ) NAME/KEY: Peptide
          ( B ) LOCATION: 1..11
          ( D ) OTHER INFORMATION: /note="amino acid 53-63 of
               desulpahtohirudin P6 (EP 347376)"

( i x ) FEATURE:
          ( A ) NAME/KEY: Modified-site
          ( B ) LOCATION: 9
          ( D ) OTHER INFORMATION: /note="The tyrosine may be
               esterified with sulphuric or phosphoric acid"

( x i ) SEQUENCE DESCRIPTION: SEQ ID NO: 3:

Asp Phe Asp Pro Ile Pro Glu Glu Tyr Leu Ser
1               5                   10

( 2 ) INFORMATION FOR SEQ ID NO: 4:

( i ) SEQUENCE CHARACTERISTICS:
          ( A ) LENGTH: 12 amino acids
          ( B ) TYPE: amino acid
          ( C ) STRANDEDNESS: single
          ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: C-terminal ( v i ) ORIGINAL SOURCE:
          ( A ) ORGANISM: Hirudo medicinalis ( i x ) FEATURE:
          ( A ) NAME/KEY: Peptide
          ( B ) LOCATION: 1..12

( D ) OTHER INFORMATION: /note="amino acid 51-62 of
desulphatohirudin P18 (EP 347376)"

( x i ) SEQUENCE DESCRIPTION: SEQ ID NO: 4:

Asp Phe Glu Glu Phe Ser Leu Asp Asp Ile Glu Gln
1               5                       10

( 2 ) INFORMATION FOR SEQ ID NO: 5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: C-terminal ( i x ) FEATURE:
        ( A ) NAME/KEY: Peptide
        ( B ) LOCATION: 1..16

( i x ) FEATURE:
        ( A ) NAME/KEY: Region
        ( B ) LOCATION: 1..5
        ( D ) OTHER INFORMATION: /note="synthetic linker"

( i x ) FEATURE:
        ( A ) NAME/KEY: Region
        ( B ) LOCATION: 6..16
        ( D ) OTHER INFORMATION: /note="C-terminal amino acids
54-64 of desulphatohirudin HV1"

( x i ) SEQUENCE DESCRIPTION: SEQ ID NO: 5:

Gly Gly Gly Gly Asn Gly Asp Phe Glu Glu Ile Pro Glu Glu Tyr Leu
1               5                       10                      15

( 2 ) INFORMATION FOR SEQ ID NO: 6:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: C-terminal ( i x ) FEATURE:
        ( A ) NAME/KEY: Domain
        ( B ) LOCATION: 4..14
        ( D ) OTHER INFORMATION: /label=hirudin
/ note="hirudin(54-64)"

( i x ) FEATURE:
        ( A ) NAME/KEY: Modified-site
        ( B ) LOCATION: 1
        ( D ) OTHER INFORMATION: /note="Xaa =4-amino-butyric acid"

( i x ) FEATURE:
        ( A ) NAME/KEY: Modified-site
        ( B ) LOCATION: 2
        ( D ) OTHER INFORMATION: /note="Xaa =6-amino-caproic acid"

( x i ) SEQUENCE DESCRIPTION: SEQ ID NO: 6:

```
Xaa  Xaa  Asn  Gly  Asp  Phe  Glu  Glu  Ile  Pro  Glu  Glu  Tyr  Leu
 1              5                        10
```

( 2 ) INFORMATION FOR SEQ ID NO: 7:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: misc_recomb
        ( B ) LOCATION: 1..25
        ( D ) OTHER INFORMATION: /organism="synthetical"
            / note="DNA coding for C-terminus of eglin"

( i x ) FEATURE:
        ( A ) NAME/KEY: misc_recomb
        ( B ) LOCATION: 26..55
        ( D ) OTHER INFORMATION: /organism="synthetical"
            / note="DNA coding for spacer"

( x i ) SEQUENCE DESCRIPTION: SEQ ID NO: 7:

```
TATAGTTAAC  CATGTTCCGC  ATGTTGGTGG  TGGCACTAAG  GGTGGCGGTG  GCAAC        55
```

( 2 ) INFORMATION FOR SEQ ID NO: 8:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: misc_recomb
        ( B ) LOCATION: complement (1..9)
        ( D ) OTHER INFORMATION: /organism="synthetical"
            / note="linker"

( i x ) FEATURE:
        ( A ) NAME/KEY: misc_recomb
        ( B ) LOCATION: complement (10..12)
        ( D ) OTHER INFORMATION: /organism="synthetical"
            / note="stop codon"

( i x ) FEATURE:
        ( A ) NAME/KEY: misc_recomb
        ( B ) LOCATION: complement (13..45)
        ( D ) OTHER INFORMATION: /organism="synthetical"
            / note="(-) DNA coding for hirudin(54-64)"

( i x ) FEATURE:
        ( A ) NAME/KEY: misc_recomb
        ( B ) LOCATION: complement (46..61)
        ( D ) OTHER INFORMATION: /organism="synthetical"
            / note="(-)DNA of last part of spacer
              ( o v e r l a p p i n g )"

( x i ) SEQUENCE DESCRIPTION: SEQ ID NO: 8:

```
TATAGGATCC  TAGAGGTACT  CTTCAGGGAT  CTCTTCGAAA  TCACCGTTGC  CACCGCCACC    60
C                                                                        61
```

( 2 ) INFORMATION FOR SEQ ID NO: 9:

( i ) SEQUENCE CHARACTERISTICS:
( A ) LENGTH: 276 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i i i ) ANTI-SENSE: NO ( v i i ) IMMEDIATE SOURCE:
( B ) CLONE: pPL.Mu.eglin-hir ( i x ) FEATURE:
( A ) NAME/KEY: CDS
( B ) LOCATION: 1..276
( D ) OTHER INFORMATION: /product="fusion protein"

( i x ) FEATURE:
( A ) NAME/KEY: misc_feature
( B ) LOCATION: 1..213
( D ) OTHER INFORMATION: /product="eglin"

( i x ) FEATURE:
( A ) NAME/KEY: misc_feature
( B ) LOCATION: 214..240
( D ) OTHER INFORMATION: /product="spacer"

( i x ) FEATURE:
( A ) NAME/KEY: misc_feature
( B ) LOCATION: 241..276
( D ) OTHER INFORMATION: /product="hirudin(54-64)"

( x i ) SEQUENCE DESCRIPTION: SEQ ID NO: 9:

| ATG | ACT | GAA | TTT | GGT | TCT | GAA | CTG | AAA | TCT | TTC | CCA | GAA | GTT | GTT | GGT | 48 |
| Met | Thr | Glu | Phe | Gly | Ser | Glu | Leu | Lys | Ser | Phe | Pro | Glu | Val | Val | Gly | |
| 1 | | | | 5 | | | | | 10 | | | | | 15 | | |

| AAA | ACT | GTT | GAC | CAG | GCT | CGT | GAA | TAC | TTC | ACT | CTG | CAT | TAC | CCG | CAG | 96 |
| Lys | Thr | Val | Asp | Gln | Ala | Arg | Glu | Tyr | Phe | Thr | Leu | His | Tyr | Pro | Gln | |
| | | | 20 | | | | | 25 | | | | | 30 | | | |

| TAC | GAC | GTT | TAC | TTC | CTG | CCG | GAA | GGT | TCT | CCT | GTT | ACT | CTG | GAC | CTG | 144 |
| Tyr | Asp | Val | Tyr | Phe | Leu | Pro | Glu | Gly | Ser | Pro | Val | Thr | Leu | Asp | Leu | |
| | | 35 | | | | | 40 | | | | | 45 | | | | |

| CGT | TAC | AAC | CGT | GTT | CGT | GTT | TTC | TAC | AAC | CCA | GGT | ACT | AAC | GTT | GTT | 192 |
| Arg | Tyr | Asn | Arg | Val | Arg | Val | Phe | Tyr | Asn | Pro | Gly | Thr | Asn | Val | Val | |
| | 50 | | | | | 55 | | | | | 60 | | | | | |

| AAC | CAT | GTT | CCG | CAT | GTT | GGT | GGT | GGC | ACT | AAG | GGT | GGC | GGT | GGC | AAC | 240 |
| Asn | His | Val | Pro | His | Val | Gly | Gly | Gly | Thr | Lys | Gly | Gly | Gly | Gly | Asn | |
| 65 | | | | | 70 | | | | | 75 | | | | | 80 | |

| GGT | GAT | TTC | GAA | GAG | ATC | CCT | GAA | GAG | TAC | CTC | TAG | | | | | 276 |
| Gly | Asp | Phe | Glu | Glu | Ile | Pro | Glu | Glu | Tyr | Leu | | | | | | |
| | | | | 85 | | | | | 90 | | | | | | | |

( 2 ) INFORMATION FOR SEQ ID NO: 10:

( i ) SEQUENCE CHARACTERISTICS:
( A ) LENGTH: 91 amino acids
( B ) TYPE: amino acid
( D ) TOPOLOGY: linear ( i i ) MOLECULE TYPE: protein ( x i ) SEQUENCE DESCRIPTION: SEQ ID NO: 10:

| Met | Thr | Glu | Phe | Gly | Ser | Glu | Leu | Lys | Ser | Phe | Pro | Glu | Val | Val | Gly |
| 1 | | | | 5 | | | | | 10 | | | | | 15 | |

| Lys | Thr | Val | Asp | Gln | Ala | Arg | Glu | Tyr | Phe | Thr | Leu | His | Tyr | Pro | Gln |

```
                        20                        25                          30
Tyr  Asp  Val  Tyr  Phe  Leu  Pro  Glu  Gly  Ser  Pro  Val  Thr  Leu  Asp  Leu
               35                        40                         45

Arg  Tyr  Asn  Arg  Val  Arg  Val  Phe  Tyr  Asn  Pro  Gly  Thr  Asn  Val  Val
     50                        55                        60

Asn  His  Val  Pro  His  Val  Gly  Gly  Gly  Thr  Lys  Gly  Gly  Gly  Gly  Asn
65                            70                   75                         80

Gly  Asp  Phe  Glu  Glu  Ile  Pro  Glu  Glu  Tyr  Leu
                    85                        90
```

( 2 ) INFORMATION FOR SEQ ID NO: 11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: C-terminal ( v i ) ORIGINAL SOURCE:
        ( A ) ORGANISM: Hirudo medicinalis ( i x ) FEATURE:
        ( A ) NAME/KEY: Peptide
        ( B ) LOCATION: 1..10
        ( D ) OTHER INFORMATION: /note="amino acid 55-64 of
            desulpahtohirudin HV1 (EP 142860)"

( x i ) SEQUENCE DESCRIPTION: SEQ ID NO: 11:

```
Asp  Phe  Glu  Glu  Ile  Pro  Glu  Glu  Tyr  Leu
1                    5                       10
```

PEPTIDE DERIVATIVES CORRESPONDING TO THE CARBOXY TERMINAL SEQUENCE OF HIRUDIN

This application is a 371 of PCT/EP93/00908, filed 15 Apr. 1993.

The invention relates to novel peptide derivatives which have activity as enzyme inhibitors, in particular as inhibitors of thrombin. The invention relates also to methods for the production of such enzyme inhibitors, to pharmaceutical compositions containing the latter and to their use as anticoagulant agents.

Accordingly, the present invention provides a compound of the formula I

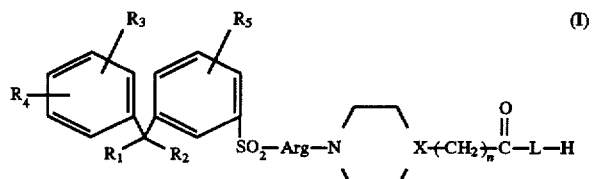

in which $R^1$ and $R^2$ are hydrogen, $C_1$–$C_4$ alkyl or are linked to form $C_3$–$C_7$ cycloalkyl and $R^3$, $R^4$ and $R^5$ are the same or different and are hydrogen, $C_1$–$C_4$ alkyl, hydroxy, $OR^6$, $SR^6$, halogen, $NR^7R^8$, $NO_2$, CN, $CONR^7R^8$ or $CO_2R^9$ wherein $R^6$ is $C_1$–$C_4$ alkyl or $C_7$–$C_{10}$ aralkyl and $R^7$, $R^8$ and $R^9$ are the same or different and are hydrogen, $C_1$–$C_4$ alkyl or $C_7$–$C_{10}$ aralkyl or $R^7$ and $R^8$ together with the nitrogen atom to which they are bound form 5 or 6 membered azacycloalkyl or oxazacycloalkyl; Arg is arginine [NH—CH(CH$_2$CH$_2$CH$_2$NH—C(=NH)—NH$_2$)—CO]; X is methine CH or nitrogen; n is an integer from 0 to 7; L is a peptide linker, and H is the carboxy terminal end of hirudin, and salts thereof.

Within the scope of the present description, the definitions used hereinbefore and hereinafter have preferably the following meanings:

$C_1$–$C_4$ Alkyl is, for example, corresponding unbranched alkyl such as ethyl, n-propyl or, especially, methyl. $C_3$–$C_7$ Cycloalkyl is, for example, cyclopentyl or cyclohexyl. Halogen is, for example, fluoro, chloro or bromo. $C_7$–$C_{10}$ Aralkyl is, for example, phenyl-$C_1$–$C_4$-alkyl such as 2-phenylethyl or, in particular, benzyl. 5 or 6 membered azacycloalkyl is, for example, pyrrolidyl or piperidyl while 5 or 6 membered oxazacycloalkyl is especially morpholyl.

The peptide linker L comprises 3 to 7 amino acids which may be naturally occurring, more especially genetically encoded, amino acids or synthetic amino acids. Because the role of this portion of the molecule is to provide a bridge between the "N-terminal" aryl moiety and the C-terminal hirudin sequence the length rather than the structure of the linker is of importance. Therefore, the choice of the amino acids to be included into the linker is not crucial. However, in order to avoid any undesired counteraction between the side chain of linker amino acids and amino acids present in the C-terminal hirudin portion of the molecules it is preferred to predominantly (or exclusively) choose neutral amino acids (i.e. amino acids which do not include strongly polar functional groups in their side chains such as carboxy, amino or guanidino groups) for the construction of the linker L. It is also preferred to select amino acids which are devoid of bulky side chains. Examples of amino acids which are useful as part of the linker L are naturally occurring or synthetic ω-amino carboxylic acids such as glycine, β-alanine, 4-amino butyric acid, 5-amino pentanoic acid, 6-amino hexanoic acid, 11-amino undecanoic acid, and the like, furthermore other neutral amino acids such as alanine, serine, threonine, glutamine, asparagine, phenylglycine, phenylalanine, and the like. It is also possible to include few, especially one, polar amino acids in the peptide chain of the linker L, such as aspartic acid, glutamic acid, lysine, histidine and the like. The linker L may also include at its C-terminal part one amino acid or a few, such as two or three, amino acids which in the hirudin molecule from which the C-terminal radical H is taken precede said C-terminal part. Especially preferred are linkers L which consist of one or more ω-amino carboxylic acids, in particular glycine, 4-amino-butyric acid or 6-amino-caproic acid, and, optionally, one or more, especially one, neutral amino acids, e.g. asparagine. The amino acids in the linker L are linked to each other by means of carboxy amide bonds (peptide bonds) as is the first ("N-terminal") amino acid of L via its amino group to the preceding carbonyl group —C(=O)— (see formula (I)) and the last ("C-terminal") amino acid via its carboxy group to the amino group of the following first amino acid of the radical H.

It has been found that the distance between the arginine residue Arg and the first amino acid of the C-terminal radical H is of prime importance. In order to secure maximal antithrombotic activity of the compounds according to the invention the backbone chain linking the carbonyl group of arginine Arg and the first amino acid of the C-terminal radical H has to comprise a definite number of atoms (or bonds). Especially, the backbone chain (II) deemed by the formula

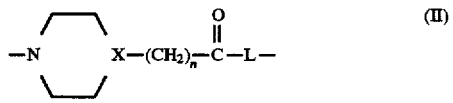

comprises about 18 to about 28, in particular about 22 to about 26, atoms.

The carboxy terminal end of hirudin is known to be involved in thrombin binding. It is to be understood that the carboxy terminal end of hirudin H (see formula (I)) comprises the corresponding terminal end of any of the known hirudins and hirullins (derivable from different leech species), such as hirudin variants HV1, HV2, HV3 (PA), and other variants, for example those described by M. Scharf et al. [FEBS Lett. 255, 105–110 (1989)] and described in European Patent Applications Nos. 347376 (variants P6 and P18) and 373767, including desulphated variants of those hirudins comprising a tyrosine sulphate residue and variants in which the tyrosine sulphate residue is replaced by a tyrosine phosphate residue. Also included are derivatives of the carboxy terminal end of hirudin in which one or more, especially one to three, amino acids have been replaced by other amino acids, which derivatives retain the binding affinity to thrombin. It has been shown by M. Scharf et al. (supra) that there are conserved or invariable amino acid regions which are found in all known hirudins. Such regions can also be found in the corresponding carboxy terminal ends. For example, all hirudins contain an aspartic acid-phenyl alanine dipeptide conserved region at a distance of about 9–11 amino acids from the hirudin C-terminus. According to the numbering of M. Scharf et al. (supra) these are amino acids 55–56 of hirudin. Whenever used in the context of the present specification the term "carboxy terminal end of hirudin" is intended to comprise the C-terminal part starting with amino acid 55 and ending at the ultimate or penultimate amino acid of hirudin. Examples of such carboxy terminal parts of hirudin are derived from hirudins HV1, HV2, HV3, P6 and P18 having the sequences (cf. SEQ ID NO:1-4)

Asp Phe Glu Glu Ile Pro Glu Glu Z Leu Gln (III),

Asp Phe Glu Pro Ile Pro Glu Asp Ala Z Asp Glu (IV),

Asp Phe Asp Pro Ile Pro Glu Glu Z Leu Ser (V), and

Asp Phe Glu Glu Phe Ser Leu Asp Asp Ile Glu Glu (VI), wherein Z is Tyr, Tyr(SO₃H) or Tyr(PO₃H₂), in the latter two cases the hydroxy group of tyrosine being esterified with sulphuric acid and phosphoric acid, respectively, and in which the ultimate amine acid (e.g. Gln in formula (III)) may be absent. The preferred carboxy terminal end H according to the invention is that of formula (III) wherein Z is Tyr and the ultimate glutamine residue is optionally lacking.

In a preferred embodiment of the present invention the "C-terminal" peptidic region L-H of the compounds of the formula I has the sequence (cf. SEQ ID NO:5)

Gly Gly Gly Gly Asn Gly Asp Phe Glu Glu Ile Pro Glu Glu Tyr Leu (IIIa).

or the sequence (cf. SEQ ID NO:6)

Gab Aca Asn Gly Asp Phe Glu Glu Ile Pro Glu Glu Tyr Leu (IVa);

wherein Gab designates 4-amino-butyric acid and Aca designates 6-amino-caproic acid.

The invention relates also to the salts, especially the pharmaceutically acceptable non-toxic salts, of the compounds according to the invention. The compounds according to the invention can form acid addition salts, for example with inorganic acids, especially mineral acids, for example hydrochloric acid, sulphuric acid or phosphoric acid, or salts with organic carboxylic, sulphonic or sulpho acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, also amino acids, as well as methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid, or with other acidic organic compounds, such as ascorbic acid. The compounds according to the invention can also form metal or ammonium salts, such as alkali metal and alkaline earth metal salts, for example sodium, potassium, magnesium or calcium salts, as well as ammonium salts with ammonia or suitable organic amines, there being suitable for the salt formation especially aliphatic, cycloaliphatic, cycloaliphatic-aliphatic or araliphatic primary, secondary or tertiary mono-, di- or poly-amines, and also heterocyclic bases, such as lower alkylamines, for example triethylamine, hydroxy-lower alkylamines, for example 2-hydroxyethylamine, bis-(2-hydroxyethyl)-amine, 2-hydroxyethyldiethylamine or tri-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine and also bases of the pyridine type, for example pyridine, collidine or quinoline. The compounds according to the invention can, in addition, form internal salts. For isolation or purification it is also possible to use salts that are not pharmaceutically suitable. Only the pharmaceutically acceptable non-toxic salts, however, are used therapeutically, and these are therefore preferred.

The compounds of the formula I and the pharmaceutically acceptable salts thereof represent bifunctional thrombin inhibitors consisting of a "N-terminal" low-molecular weight thrombin inhibitor moiety linked through spacer sequences with the thrombin-binding carboxy terminal region of hirudin. These bifunctional thrombin inhibitors exhibit a high specific activity in mammals including humans against thrombin and therefore these compounds are useful for the medical treatment or prevention of thrombosis or diseases caused by thrombosis or can be used for the determination of thrombin in blood as diagnostic reagents.

The invention relates especially to a compound of the formula (I) in which $R^1$ and $R^2$ are each $C_1$–$C_4$ alkyl, $R^3$, $R^4$ and $R^5$ are each hydrogen; Arg is arginine; X is methine CH or nitrogen; n is an integer from 0 to 7; L is a peptide linker comprising 3 to 6 amino acids selected from the group consisting of a $C_2$–$C_{12}$-ω-amino carboxylic acid, alanine, serine, threonine, glutamine, asparagine, phenylglycine or phenylalanine; and H is the carboxy terminal end of hirudin starting with amino acid 55 and ending at the ultimate or penultimate amino acid of hirudin, a desulphated variant of such a hirudin comprising a tyrosine sulphate residue, a variant of such a hirudin in which the tyrosine sulphate residue is replaced by a tyrosine phosphate residue, or a derivative thereof in which 1–3 amino acids are replaced by other amino acids, which derivatives retain the binding affinity to thrombin; wherein the backbone chain (II) defined by the formula

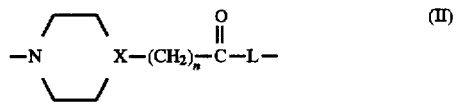

comprises about 18 to about 28, in particular about 22 to about 26, atoms; and pharmaceutically acceptable salts thereof.

More especially, the invention relates to a compound of the formula (I) in which $R^1$ and $R^2$ represent each methyl, $R^3$, $R^4$ and $R^5$ are each hydrogen; Arg is arginine; X is methine CH; n is 2; L is a peptide linker comprising 3 to 6 amino acids selected from the group consisting of a $C_2$–$C_{12}$-ω-amino carboxylic acid and asparagine; and H is the carboxy terminal end of hirudin variant HV1 starting with amino acid 55 and ending at the ultimate or penultimate amino acid of hirudin HV1 or a desulphated variant thereof; wherein the backbone chain (II) defined by the formula

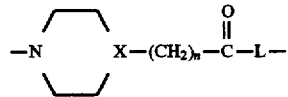

comprises about 22 to about 26 atoms; and pharmaceutically acceptable salts thereof.

Most preferred is a compound of the formula (I) in which $R^1$ and $R^2$ each represent methyl, $R^3$, $R^4$ and $R^5$ are each hydrogen; Arg is arginine; X is methine CH; n is 2; L is a peptide linker comprising 3 to 6 amino acids selected from the group consisting of 4-amino-butyric acid, 5-amino-caproic acid, glycine and asparagine; and H is the carboxy terminal end of desulphatohirudin variant HV1 starting with amino acid 55 and ending at the penultimate amino acid of hirudin HV1 wherein the backbone chain (II) defined by the formula

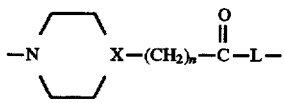

comprises 22 to 26 atoms; and pharmaceutically acceptable salts thereof.

The most preferred compounds according to the invention are those described in the examples.

The compounds according to the invention can be manufactured in a manner known per se.

The process for the production of a compound of the formula I comprises, for example, reacting an amide bond forming first fragment of a compound of formula I with a second amide bond forming fragment of a compound of formula I, said first fragment and said second fragment being complementary to one another such that an amide bond is formed between said first and second fragments to result in said compound of formula I, one of said first and second fragments containing a reactive free carboxy group and sulphoxy group, respectively, or a reactive carboxylic acid or sulphonic acid derivative thereof, and the other of said first and second fragments containing a free amino group or a reactive derivative thereof, wherein free functional groups in the mentioned fragments, with the exception of the two groups participating in the reaction, are, if necessary, in protected form, and removing protecting groups which may be present, and, if desired, converting a salt obtainable in accordance with the process into the free compound and/or converting a free compound obtainable in accordance with the process into a salt.

According to the process according to the invention, the last stage of the reaction includes the formation of an amide bond at any possible position within the molecule of the formula I. The mentioned fragment that contains a free carboxy group may be any one of the following compounds of the formula VII-X

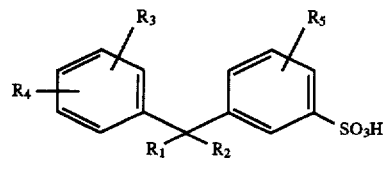

(VII)

H—Arg—OH (VIII)

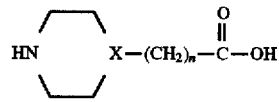

(IX)

H—L'—OH (X)

wherein H-L'-OH defines a amino acid sequence consisting of part of amino acids of linker L, or consisting of the linker L optionally including additional amino acids of the carboxy terminal end of hirudin H and wherein the C-terminal amino acid has a free carboxy group, wherein free functional groups not participating in the reaction are, if necessary, in protected form.

The fragment that contains a free amino group may be a single amino acid (i.e. the C-terminal amino acid of the compound of the formula I), a di-, oligo- or poly-peptide consisting of at least part of the amino acids of the carboxy terminal part of hirudin H optionally additionally including all or part of the amino acids of the linker L or is one of the following fragments XI or XII

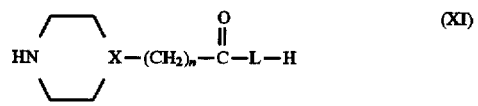

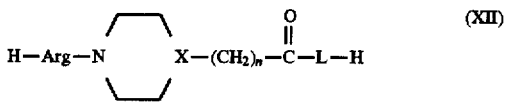

wherein, in the fragment of the formula (XII), the α-amino group of arginine Arg is in the free form.

Preferably, the reaction is carried out by reacting a reactive carboxylic acid or sulphonic acid derivative of the one fragment with the complementary fragment that contains a free amino group, it being possible for the derivatisation of the carboxy group of the carboxylic acid fragment to be effected in situ. Suitable synthetic methods are described, for example, in M. Bodanszky, Peptide Chemistry, Springer Verlag, Berlin 1988, and in E. Atherton and R. C. Sheppard, Solid Phase Peptide Synthesis, IRL press, Oxford, 1989.

Reactive carboxylic acid and sulphonic acid derivatives are especially reactive activated esters or reactive anhydrides, and also reactive cyclic amides; as mentioned, reactive carboxylic acid derivatives can be formed in situ.

Activated esters of acids are especially esters that are unsaturated at the linking carbon atom of the esterifying radical, for example of the vinyl ester type, such as true vinyl esters (which can be obtained, for example, by the transesterification of a corresponding ester with vinyl acetate; activated vinyl ester method), carbamoylvinyl esters (which can be obtained, for example, by treating the corresponding acid with an isoxazolium reagent; 1,2-oxazolium or Woodward method), or 1-lower alkoxyvinyl esters (which can be obtained, for example, by treating the corresponding acid with a lower alkoxyacetylene; ethoxyacetylene method), or esters of the amidino type, such as N,N'-disubstituted amidino esters (which can be obtained, for example, by treating the corresponding acid with a suitable N,N'-disubstituted carbodiimide, for example N,N'-diisopropyl- or N,N'-dicyclohexyl-carbodiimide; carbodiimide method), or N,N-disubstituted amidino esters (which can be obtained, for example, by treating the corresponding acid with an N,N-disubstituted cyanamide; cyanamide method). Activated esters are also, for example, suitable aryl esters, especially phenyl esters suitably substituted by electronattracting substituents (which esters can be obtained, for example, by treating the corresponding acid with a suitably substituted phenol, for example 4-nitrophenol, 4-methylsulfonylphenol, 2,4,5-trichlorophenol, 2,3,4,5,6-pentachlorophenol, pentafluorophenol or 4-phenyldiazophenol, in the presence of a condensing agent, such as N,N'-dicyclohexylcarbodiimide; activated aryl esters method) cyanomethyl esters (which can be obtained, for example, by treating the corresponding acid with chloroacetonitrile in the presence of a base; cyanomethyl esters method), suitable thioesters, especially phenylthio esters that are unsubstituted or substituted, for example, by nitro (which can be obtained, for example, by treating the corresponding acid with a thiophenol that is unsubstituted or substituted, for example, by nitro, inter alia with the aid of the anhydride or carbodiimide method; activated thiol esters method), or amino or amido esters (which can be obtained, for example, by treating the corresponding acid with an N-hydroxyamino or N-hydroxyamido compound, for example N-hydroxysuccinimide, N-hydroxypiperidine, N-hydroxyphthalimide or 1-hydroxy-1H-benzotriazole, for example according to the anhydride or carbodiimide method; activated N-hydroxy esters method).

Reactive acid anhydrides may be symmetrical or preferably mixed anhydrides of these acids, for example anhydrides with inorganic acids, such as acid halides, especially acid chlorides (which can be obtained, for example, by treating the corresponding acid, including sulphonic acid, with a suitable halogenating agent, such as thionyl chloride, phosphorus pentachloride or oxalyl chloride; acid chloride method); azides (which can be obtained, for example, from an acid ester by way of the corresponding hydrazide and treatment thereof with nitrous acid; azide method), anhydrides with carbonic acid semi-derivatives, such as with corresponding esters, for example carbonic acid lower alkyl semi-esters (which can be obtained, for example, by treating the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an unsubstituted or substituted lower alkanecarboxylic or phenyl-lower alkanecarboxylic acid halide, for example phenylacetic acid, pivalic acid or trifluoroacetic acid chloride; mixed carboxylic acid anhydrides method) or with organic sulfonic acids (which can be obtained, for example, by treating a salt, such as an alkali metal salt, of the corresponding acid with a suitable organic sulfonic acid halide, such as a lower alkanesulfonic or arylsulfonic acid chloride, for example methane- or p-toluene-sulfonic acid chloride; mixed sulfonic acid anhydrides method), as well as symmetrical anhydrides (which can be obtained, for example, by condensation of the corresponding acid in the presence of a carbodiimide or of 1-diethylaminopropyne; symmetrical anhydrides method).

Suitable cyclic amides are especially amides with five-membered diazacycles of aromatic character, such as amides with imidazoles, for example imidazole (which can be obtained, for example, by treating the corresponding acid with N,N'-carbonyldiimidazole; imidazolide method) or pyrazoles, for example 3,5-dimethylpyrazole (which can be obtained, for example, by way of the acid hydrazide by treatment with acetylacetone; pyrazolide method).

As mentioned, the carboxylic acid derivatives can also be formed in situ. For example, N,N'-disubstituted amidino esters can be formed in situ by reacting a mixture of the complementary fragment having the free amino group and the peptide fragment having a free carboxy group in the presence of a suitable N,N-disubstituted carbodiimide, for example N,N-diisopropyl- or N,N'-dicyclohexyl-carbodiimide. Further, amino or amido esters of acids can be formed in the presence of the amine to be acylated by reacting a mixture of the corresponding acid and amino starting materials in the presence of an N,N'-disubstituted carbodiimide, for example N,N'-dicyclohexyl- or N,N'-diisopropyl carbodiimide, and in the presence of an N-hydroxyamine or N-hydroxyamide, for example N-hydroxysuccinimide, optionally in the presence of a suitable base, for example 4-dimethylaminopyridine.

Alternatively, the process according to the invention can also be carried out by reacting a fragment having a free carboxy group with the complementary fragment in which the amino group is present in reactive form; the amino group can be activated, for example, by reaction with a phosphite, for example diethyl chlorophosphite, 1,1-phenylene chlorophosphite, ethyl dichlorophosphite, ethylene chlorophosphite or tetraethyl pyrophosphite, or with a suitable silylation agent, such as an organic halosilane, for example trimethylchlorosilane. The amino group can also be activated by bonding to halocarbonyl, for example chlorocarbonyl, or can be activated in the form of an isocyanate group.

Functional groups in the mentioned fragments which, if they are not to participate in the reaction, are advantageously in protected form, are especially carboxy, amino and hydroxy groups, and also carbamoyl and guanidino groups.

Protecting groups and the manner in which they are introduced and removed are described, for example, in "Protective Groups in Organic Chemistry", Plenum Press, London, New York 1973, in "Methoden der organischen Chemie", Houben-Weyl, 4th Edition, Vol. 15/1, Georg-Thieme-Verlag, Stuttgart 1974, and in Th. W. Greene, "Protective Groups in Organic Synthesis", John Wiley & Sons, New York 1981. It is characteristic of protecting groups that they can be readily removed, that is to say without undesired secondary reactions taking place, for example by solvolysis, reduction or photolysis.

Hydroxy-protecting groups are, for example, acyl radicals, such as unsubstituted or substituted, for example halo-substituted, lower alkanoyl, such as 2,2-dichloroacetyl, or acyl radicals of carbonic acid semi-esters, especially tert.-butoxycarbonyl, unsubstituted or substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, or formyl. Other hydroxy-protecting groups are, for example, suitable etherifying groups, such as trityl, tert.-lower alkyl, for example tert.-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having 5 or 6 ring atoms, for example 2-tetrahydrofuryl or 2-tetrahydropyranyl or corresponding thia analogues, and also unsubstituted or substituted 1-phenyl-lower alkyl, such as unsubstituted or substituted benzyl or diphenylmethyl, there being suitable as substituents of phenyl radicals, for example, halogen, such as chlorine, lower alkoxy, such as methoxy, and/or nitro. Further hydroxy-protecting groups are also organic silyl or stannyl radicals that preferably contain lower alkyl, especially methyl, and/or aryl, for example phenyl, as substituents, especially tri-lower alkylsilyl, especially trimethylsilyl, and also dimethyl-tert.-butyl-silyl, or correspondingly substituted stannyl, for example tri-n-butylstannyl.

Carboxy groups are preferably protected in esterified form, such ester groupings being readily cleavable under mild conditions. Carboxy groups protected in this manner contain as esterifying groups especially lower alkyl groups that are branched at the 1-position or suitably substituted at the 1- or 2-position. Preferred carboxy groups in esterified form are, inter alia, tert.-lower alkoxycarbonyl, for example tert.-butoxycarbonyl, α-aryl-lower alkoxycarbonyl having one or two aryl radicals, these being phenyl radicals that are unsubstituted or substituted, for example, by lower alkyl, such as tert.-lower alkyl, for example tert.-butyl, lower alkoxy, such as methoxy, hydroxy, halogen, for example chlorine, nitro and/or by phenyl, such as benzyloxycarbonyl that is unsubstituted or substituted, for example, as mentioned above, for example 4-methoxybenzyloxycarbonyl or 4-nitrobenzyloxycarbonyl, biphenylyl-lower alkoxycarbonyl in which biphenylyl substitutes the α-position, for example 2-(p-biphenylyl)-2-propoxycarbonyl, or diphenylmethoxycarbonyl that is unsubstituted or substituted, for example, as mentioned above, for example diphenylmethoxycarbonyl or di-(4-methoxyphenyl)-methoxycarbonyl, 1-lower alkoxy-lower alkoxycarbonyl, such as methoxymethoxycarbonyl, 1-methoxyethoxycarbonyl or 1-ethoxymethoxycarbonyl, 2,2-diaryl-ethoxycarbonyl in which aryl is phenyl that is unsubstituted or substituted, for example, by nitro, such as 4-nitrophenyl, such as 2,2-di-(4-nitrophenyl)-ethoxycarbonyl, wherein the two aryl, for example phenyl, radicals may also be bonded to one another, for example 2-(9-fluorenyl)-ethoxycarbonyl, 1-lower alkylthio-lower alkoxycarbonyl, such as 1-methylthiomethoxycarbonyl or 1-ethylthioethoxycarbonyl, aroylmethoxycarbonyl in which the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which each of the substituents, independently of the others, represents an aliphatic, araliphatic, cycloaliphatic or aromatic hydrocarbon radical that is unsubstituted or substituted, for example, by lower alkyl, lower alkoxy, aryl, halogen and/or by nitro, such as unsubstituted or correspondingly substituted lower alkyl, phenyl-lower alkyl, cycloalkyl or phenyl, for example 2-tri-lower alkylsilylethoxycarbonyl, such as 2-trimethylsilylethoxycarbonyl or 2-(methyl-di-(n-butyl)-silyl)-ethoxycarbonyl, or 2-triarylsilylethoxycarbonyl, such as 2-triphenylsilylethoxycarbonyl.

Preferred protected carboxy groups are, for example, tert.-lower alkoxycarbonyl, such as tert.-butoxycarbonyl, and benzyloxycarbonyl that is unsubstituted or substituted, for example, as mentioned above, such as 4-methoxy- or 4-nitrobenzyloxycarbonyl, or diphenylmethoxycarbonyl, and also 2-(trimethylsilyl)-ethoxycarbonyl.

A protected amino group can be, for example, in the form of a readily cleavable acylamino, arylmethylamino, etherified mercaptoamino, 2-acyllower alk-1-enylamino, silylamino or stannylamino group or in the form of an azido group.

In a corresponding acylamino group, acyl is, for example, the corresponding radical of an organic carboxylic acid having, for example, up to 18 carbon atoms, especially an alkanecarboxylic acid that is unsubstituted or substituted, for example, by halogen or aryl, or of benzoic acid that is unsubstituted or substituted, for example, by halogen, for example chlorine, lower alkoxy, for example methoxy, nitro, and/or by phenyl, or of a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo-2-iodo-, 2,2,2-trifluoro- or 2,2,2-trichloroacetyl, benzoyl that is unsubstituted or substituted, for example, by halogen, lower alkoxy, nitro and/or by phenyl, for example benzoyl, 4-chlorobenzoyl, 4-methoxybenzoyl or 4-nitrobenzoyl, or lower alkoxycarbonyl that is branched at the 1-position of the lower alkyl radical or suitably substituted at the 1- or 2-position, especially tert.-lower alkoxycarbonyl, for example tert.-butoxycarbonyl, lower alkenyloxycarbonyl, for example allyloxycarbonyl, α-aryl-lower alkoxycarbonyl having one or two aryl radicals that are preferably phenyl that is unsubstituted or substituted, for example, by lower alkyl, especially tert.-lower alkyl, such as tert.-butyl, lower alkoxy, such as methoxy, hydroxy, halogen, for example chlorine, nitro and/or by phenyl, such as unsubstituted or substituted benzyloxycarbonyl, for example 4-nitrobenzyloxycarbonyl, biphenylyl-lower alkoxycarbonyl in which biphenylyl substitutes the α-position, for example 2-(p-biphenylyl)-2-propoxycarbonyl), or substituted diphenylmethoxycarbonyl, for example benzhydryloxycarbonyl or di-(4-methoxyphenyl)-methoxycarbonyl, 2,2-diarylethoxycarbonyl in which aryl is phenyl that is unsubstituted or substituted, for example, by nitro, such as 4-nitrophenyl, such as 2,2-di-(4-nitrophenyl)-ethoxycarbonyl, wherein the two aryl, for example phenyl, radicals may also be bonded to one another, for example 9-fluorenyl-methoxycarbonyl, aroylmethoxycarbonyl in which the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, optionally substituted 2-phenylsulphonylethoxycarbonyl, such as 2-(4-methylsulphonylphenylsulphonyl)-ethoxycarbonyl, or 2-(tri-substituted silyl)-ethoxycarbonyl in which each of the substituents, independently of the others, is an aliphatic, araliphatic, cycloaliphatic or aromatic hydrocarbon radical that has up to 15 carbon atoms and is unsubstituted or substituted, for example, by lower alkyl, lower alkoxy, aryl, halogen or by nitro, such as corresponding unsubstituted or substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Further acyl radicals suitable as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, unsubstituted or substituted diphenylphosphoryl, for example diphenylphosphoryl, di-(phenyl-lower alkyl)-phosphoryl that is unsubstituted or substituted, for example, by nitro, for example dibenzylphosphoryl or di-(4-nitrobenzyl)-phosphoryl, unsubstituted or substituted phenoxyphenylphosphonyl, for example phenoxyphenylphosphonyl, di-lower alkylphosphinyl, for example diethylphosphinyl, or unsubstituted or substituted diphenylphosphinyl, for example diphenylphosphinyl.

In an arylmethylamino group, which may be a mono-, di- or especially tri-arylmethylamino group, the aryl radicals are especially unsubstituted or substituted phenyl radicals. Such groups are, for example, benzylamino, diphenylmethylamino and especially tritylamino.

An etherified mercapto group in an amino group protected by such a radical is especially arylthio or aryl-lower alkylthio in which aryl is especially phenyl that is unsubstituted or substituted, for example, by lower alkyl, such as methyl or tert.-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that may be used as an aminoprotecting group, acyl is, for example, the corresponding radical of a lower alkanecarboxylic acid, of a benzoic acid that is unsubstituted or substituted, for example, by lower alkyl, such as methyl or tert.-butyl, lower alkoxy, such as methoxy, halogen, such as chlorine, and/or by nitro, or especially of a carbonic acid semi-ester, such as a carbonic acid lower alkyl semi-ester. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonyl-prop-1-en-2-yl.

An amino group can also be protected in protonated form; as corresponding anions there come into consideration especially those of strong inorganic acids, such as hydrohalic acids, for example the chloride or bromide anion, or organic sulfonic acids, such as p-toluenesulfonic acid.

Preferred amino-protecting groups are acyl radicals of carbonic acid semi-esters, especially tert.-butoxycarbonyl, allyloxycarbonyl, or benzyloxycarbonyl that is unsubstituted or substituted, for example as indicated, for example 4-nitrobenzyloxycarbonyl, or diphenylmethoxycarbonyl, 9-fluorenyl-methoxycarbonyl, or 2-halo-lower alkoxycarbonyl, such as 2,2,2-trichloroethoxycarbonyl, and also trityl or formyl.

Unsubstituted carbamoyl groups are protected, for example, in the form of N-(9-xanthenyl) derivatives or in the form of N-(mono-, di- or tri-arylmethyl) derivatives, in which aryl is especially phenyl that is unsubstituted or contains up to 5 identical or different substituents, preferably lower alkyl, such as methyl, or lower alkoxy, such as methoxy. The following may be mentioned as examples of such arylmethyl protecting groups: 4-methoxybenzyl, 2,4,6-trimethoxybenzyl, diphenylmethyl, di-(4-methoxyphenyl)-methyl, di-(4-methylphenyl)-methyl and (4-methylphenyl)-([polymeric carrier]phenyl)-methyl. A preferred carbamoyl-protecting group is trityl.

Guanidino groups may be protected, for example, by protonation, or by nitro or by means of suitably substituted sulfonyl groups, such as arylsulfonyl in which aryl is phenyl that is unsubstituted or contains, for example, lower alkyl, such as methyl, or benzoheterocyclyl, such as chromanyl, that is unsubstituted or substituted, for example, by lower alkyl, such as methyl, and bonded by way of an aromatic carbon atom, such as 4-methoxyphenylsulfonyl or 2,2,5,7,8-pentamethyl-6-chromanylsulfonyl.

In this application there is to be understood by a protecting group, especially a carboxy-protecting group, also a polymeric career that is bonded to the functional group to be protected, especially to a carboxy group, which carrier is suitable especially for the so-called Merrifield peptide synthesis and can be readily removed. Such a polymeric carrier is, for example, preferably a polystyrene resin weakly crosslinked by copolymerisation with divinylbenzene, which resin carries bridging members suitable for the reversible bonding of amino acid and peptide residues. Especially in connection with the above-mentioned weakly crosslinked polystyrene resin, these bridging members are especially methylene groups that are unsubstituted or substituted and that are bonded directly to aromatic radicals of the polystyrene resin. Substituents of the methylene groups are bonded to the methylene groups preferably by ether or ester groupings and contain suitable functional groupings that together with functional groups, especially carboxy groups, of the amino acid or peptide fragment, can form protected groups, especially corresponding carboxy groups, such as esterified carboxy groups. Such bridging members are, for example, the divalent radicals of 4-methoxybenzyl alcohols optionally containing in the α-position lower alkoxy, such as methoxy, or phenyl that is unsubstituted or substituted, for example in the o- and/or p-position, for example by lower alkoxy, such as methoxy, in which 4-methoxybenzyl alcohols the carbon atom of the 4-methoxy group is bonded directly to a phenyl radical of the polystyrene resin, and the benzylic hydroxy group esterifies the carboxy function of the amino acid or of the peptide fragment.

The reaction to form the amide bond can be carried out in a manner known per se, the reaction conditions depending especially on whether and how the carboxy group that participates in the reaction has been activated, customarily in the presence of a suitable solvent or diluent or a mixture thereof, and, if necessary, in the presence of a condensing agent which, for example, if the carboxy group that participates in the reaction is present in the form of an anhydride, may also be a suitable acid-binding agent, with cooling or heating, for example in a temperature range of from approximately −30° C. to approximately +150° C., especially from +10° C. to +70° C., preferably from room temperature (approximately +20° C.) to +50° C., in a closed reaction vessel and/or in the atmosphere of an inert gas, for example nitrogen.

Customary condensing agents are, for example, carbodiimides, for example N,N'-diethyl-, N,N'-diisopropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium-3'-sulfonate and 2-tert.-butyl-5-methylisoxazolium perchlorate, a suitable acylamino compound, for example 2-ethoxy-1-ethoxycarbonyl-1,2-dihydroquinoline, furthermore a uronium compound, for example 2-(1H-benzotriazol-1-yl)-1,1,3,3-tetramethyluronium tetrafluoroborate (TBTU), or a phosphonium compound, for example benzotriazole-1-yl-oxy-tris-(dimethylamino)-phosphonium hexafluorophosphate (BOP) or benzotriazole-1-yl-oxy-pyrrolidinophosphonium hexafluorophosphate (PyBOP). Customary acid-binding agents are, for example, alkali metal carbonates or bicarbonates, for example sodium or potassium carbonate or bicarbonate (customarily together with a sulfate), or organic bases, such as customarily sterically hindered tri-lower alkylamines, for example N,N-diisopropyl-N-ethylamine.

The above-mentioned Merrifield peptide synthesis is suitable especially for a semi-automatic or fully automatic synthesis of compounds of formula I, wherein amine acids and/or peptide fragments and/or other non-peptidic moieties in which functional groups not participating in the reaction are usually in protected form are linked to one another by way of amide groupings without isolation of the peptide fragments formed. One of the functional groups, normally the terminal carboxy group present in the end peptide, is optionally bonded to a suitable polymeric carrier by a bridging member, as described. In principle this process variant is carried out analogously to the customary synthesis of peptides, care being taken that, in the already synthesised (peptide) fragment that contains the polymeric carrier moiety, the freeing, from the protected group, of the functional group that participates in the reaction, usually the terminal amine group, is in each case carried out under conditions in which the protecting groups of the functional groups not participating in the reaction are retained.

The removal of carboxy-, amine-, hydroxy-, carboxylic acid amide-, carbamoyl- and/or guanidino-protecting groups is carried out in a manner known per se, for example by means of β-elimination, solvolysis, especially hydrolysis (under acid or basic conditions), alcoholysis, acidolysis or treatment with a base, or by means of reduction, especially hydrogenolysis or chemical reduction, optionally in stages or simultaneously, it also being possible to use enzymatic methods.

Thus, tert.-lower alkoxycarbonyl, or lower alkoxycarbonyl substituted in the 2-position by an organic silyl group or in the 1-position by lower alkoxy or lower alkylthio, or unsubstituted or substituted diphenylmethoxycarbonyl, can be converted into free carboxy by acidolysis, for example by treatment with a suitable acid, such as a lower alkanecarboxylic acid which may contain halogen, for example formic acid or trifluoroacetic acid, with or without the addition of a nucleophilic compound, such as phenol or anisole. Unsubstituted or substituted benzyloxycarbonyl can be freed, for example, by hydrogenolysis, that is to say by treatment with hydrogen in the presence of a metallic hydrogenation catalyst, such as a palladium catalyst. In addition, suitably substituted benzyloxycarbonyl, such as 4-nitrobenzyloxycarbonyl, can be converted into free carboxy also by chemical reduction, for example by treatment with an alkali metal dithionite, for example sodium dithionite, or with a reducing metal, for example zinc, or a reducing metal salt, such as a chromium(II) salt, for example chromium(II) chloride, usually in the presence of a hydrogen donor that, together with the metal, is capable of producing nascent hydrogen, such as an acid, especially a suitable carboxylic acid, such as a lower alkanecarboxylic acid that is unsubstituted or substituted, for example, by hydroxy, for example acetic acid, formic acid, glycolic acid, diphenylglycolic acid, lactic acid, mandelic acid, 4-chloromandelic acid or tartaric acid, or an alcohol or thiol, water preferably being added. 2,2-Diarylethoxycarbonyl or 2-(9-fluorenyl)-ethoxycarbonyl groups can be cleaved under mild basic conditions, for example by treatment with piperidine. By treatment with a reducing metal or metal salt, as described above, it is also possible to convert 2-halo-lower alkoxycarbonyl (optionally after conversion of a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl also by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid yielding the fluoride anion, such as an alkali metal fluoride, for example sodium or potassium fluoride, in the presence of a macrocyclic polyether ("crown ether"), or with a fluoride or an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulfoxide or N,N-dimethylacetamide.

A protected amine group is freed in a manner known per se and, depending on the nature of the protecting groups, by various methods, but preferably by solvolysis or reduction. 2-Halo-lower alkoxycarbonylamino (optionally after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert.-lower alkoxycarbonylamino or 2-trisubstituted silylethoxycarbonylamino can be cleaved by treatment with a suitable acid, such as a lower alkanecarboxylic acid that is unsubstituted or substituted, for example, by halogen, such as fluorine, for example formic acid or trifluoroacetic acid, and 2,2-diarylethoxycarbonylamino, such as 2,2-di-(4-nitrophenyl)-ethoxycarbonylamino, 2-(4-methylsulphonylphenylsulphonyl)-ethoxycarbonyl and also 9-fluorenyl-methoxycarbonylamino by treatment with a suitable base, such as an aliphatic, preferably secondary, amine, for example piperidine. The amino group can be freed from unsubstituted or substituted benzyloxycarbonylamino, for example, by hydrogenolysis, that is to say by treatment with hydrogen in the presence of a suitable hydrogenation catalyst, such as a palladium catalyst, from unsubstituted or substituted triarylmethylamino or formylamino, for example, by treatment with an acid, such as a mineral acid, for example hydrochloric acid, or an organic acid, for example formic, acetic or trifluoroacetic acid, in the presence or absence of water, and from an organic silylamino group, for example, by hydrolysis or alcoholysis. An amino group protected by 2-haloacetyl, for example 2-chloroacetyl, can be freed, for example, by treatment with thiourea in the presence of a base, or with a thiolate salt, such as an alkali metal thiolate, of thiourea, and by subsequent solvolysis, such as alcoholysis or hydrolysis, of the resulting condensation product. An amino group protected by 2-substituted silylethoxycarbonyl can also be convened into the free amino group by treatment with a salt of hydrofluoric acid yielding fluoride anions, as described above in connection with the freeing of a correspondingly protected carboxy group.

Amino protected in the form of an azido group can be converted into free amino, for example, by reduction, for example by catalytic hydrogenation with hydrogen in the presence of a hydrogenation catalyst, such as platinum oxide, palladium or Raney nickel, or alternatively by treatment with zinc in the presence of an acid, such as acetic acid. The catalytic hydrogenation can preferably be carried out in an inert solvent, such as a halogenated hydrocarbon, for example methylene chloride, or alternatively in water or a mixture of water and an organic solvent, such as an alcohol or dioxan, at approximately from 20° C. to 25° C., or alternatively with cooling or heating.

A hydroxy group protected by a suitable acyl group, an organic silyl group or by unsubstituted or substituted 1-phenyl-lower alkyl can be freed analogously to a correspondingly protected amino group. A hydroxy group protected by 2,2-dichloroacetyl can be freed, for example, by basic hydrolysis, and a hydroxy group etherified by tert.-lower alkyl, for example tert.-butyl, or by a 2-oxa- or 2-thia-aliphatic or -cycloaliphatic hydrocarbon radical can be freed by acidolysis, for example by treatment with a mineral acid or a strong carboxylic acid, for example trifluoroacetic acid.

A carboxylic acid amide group protected by 9-xanthenyl can be freed, for example, by treatment with hydrogen bromide in glacial acetic acid or with hydrogen fluoride in the presence of anisole. A carboxylic acid amide group protected by mono-, di- or tri-arylmethyl can be freed, for example, by treatment with hydrogen fluoride in the presence of anisole; furthermore, a diphenylmethyl protecting group can be removed, for example, by hydrogenolysis in the presence of a palladium-on-carbon catalyst, and a di-(4-methoxyphenyl)-methyl protecting group or a 2,4,6-trimethoxybenzyl protecting group can be removed, for example, by treatment with trifluoroacetic acid.

Guanidino groups protected by organic sulfonyl groups, such as 4-methylphenylsulfonylguanidino or 2,2,5,7,8- pentamethyl-6-chromanylsulfonylguanidino, can be freed, for example, by treatment with a suitable acid, such as trifluoroacetic acid. Guanidino groups protected by nitro can be freed, for example, by hydrogenolysis in the presence of palladium-on-carbon catalyst.

A protected functional group, especially a corresponding carboxy group, in which the protecting group simultaneously acts as a carrier material in the mentioned Merrifield peptide synthesis, can be cleaved in a manner known per se, for example as described above. A correspondingly esterified carboxy group that is bonded to the polymeric carrier material by way of a suitable bridging member is cleaved in accordance with the nature of the bridging member. For example, a carboxy group bonded to the polymeric carrier material by way of an ester grouping having an activated benzylic bridging member, for example a 4-methoxybenzyloxycarbonyl group, in which the carbon atom of the methoxy group is bonded, for example, to a phenyl radical of the polystyrene resin weakly crosslinked with divinylbenzene, can be freed analogously to the above-mentioned unsubstituted or substituted benzyloxycarbonyl groups, for example by treatment with a suitable acid, such as trifluoroacetic acid.

If desired, if several protected functional groups are present, the protecting groups can be so selected that more than one of these protecting groups can be removed at the same time, for example by acidolysis, such as by treatment with trifluoroacetic acid or formic acid, or by reduction, such as by treatment with zinc and acetic acid, or with hydrogen and a hydrogenation catalyst, such as a palladium-on-carbon catalyst.

The carboxy terminal end of hirudin be manufactured in a manner known per se. The desired fragment can be synthesized for example on a peptide synthesizer, directly expressed in a host or cleaved from an expressed precursor protein or a fusion protein with enzymes or chemical agents.

Normally, heterologous proteins with less than 20 amino acids cannot be expressed and isolated in sufficient mounts from natural hosts like E. coli. A possible method for the expression of small proteins such as the carboxyterminal fragment of hirudin consists in fusing the small protein in question in frame to another protein thus creating a fusion protein. Several methods have been developed to liberate the desired protein from its fusion partner (Nishikawa et al., Protein Engineering 1, 487-492 (1987); Gardella et al., J. Biol. Chem. 265, 15854-15859, (1990); Altman et al., Protein Engineering 4, 593-600 (1991)). Possible hosts are fungi like yeasts or bacteria like E. coli.

Suitable endogenous fusion partners are highly expressed proteins. Preferred are proteins like eglin, β-galactosidase, β-lactamase, several proteins involved in the tryptophan synthesis in E. coli, protein A or chloramphenicol acetyl transferase.

The desired carboxyterminal fragment of hirudin has to be removed from the fusion partner after expression and purification of the fusion protein. If there is no natural cleavage site between the desired fragment and the fusion partner, this is generally done by means of a linker sequence linking the desired fragment to the fusion partner and containing a cleavage site which can selectively be cleaved by chemical or enzymatic means. Such cleavage sites include, for example, a methionyl radical which is susceptible to the attack of cyanogen bromide, a polypeptide chain including the tetrapeptidyl radical Asp-Asp-Asp-Lys which is cleaved by enterokinase after Lys or any other cleavage site susceptible to a specific cleavage with enzymes like V8 protease, trypsin, peptidase yscα or yscF.

The fusion proteins can be prepared in a manner known per se by recombinant DNA technique comprising culturing a transformed host under conditions which allow expression and isolation of the fusion protein. More specifically, the desired compounds are manufactured by

- providing an expression vector comprising an expression cassette containing a DNA sequence coding for said fusion protein under the control of a strong promoter,
- transferring the expression vector into a recipient host,
- culturing the transformed host under conditions which allow expression of the fusion protein, and
- isolating the fusion protein.

The expression vector can be prepared e.g. by normal recombinant DNA techniques.

If the peptide linker (L) between the hirudin fragment (H) and the radical of the formula (XIII)

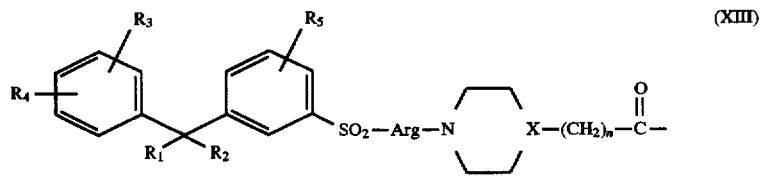

wherein residues $R_1$–$R_5$ and n have the meanings as defined above, contains only genetically encoded amino acids, the expression vector can comprise a DNA coding for the complete peptide linker-hirudin fragment (-L-H). The N-terminus of the isolated peptide linker-hirudin fragment can be linked directly to the radical of the formula (XIII). If the peptide linker contains non-genetically encoded amino acids (e.g. 4-amino-butyric acid and 6-amino-caproic acid) the isolated hirudin fragment has to be attached to these non-genetically encoded amino acids and subsequently to the radical of the formula (XIII) or the non-genetically encoded amino acids have to be attached to the radical of the formula (XIII) and subsequently to the isolated hirudin fragment.

Salts of compounds of formula I can be manufactured in a manner known per se. For example, salts of compounds of formula I that contain more acidic than basic groups can be formed, for example, by treatment with metal compounds, such as alkali metal salts of suitable organic carboxylic acids, for example the sodium salt of ethylcaproic acid, or with inorganic alkali metal or alkaline earth metal salts, for example sodium bicarbonate, or with ammonia or a suitable organic amine, there preferably being used stoichiometric amounts or only a small excess of the salt-forming agent. Acid addition salts of compounds of formula I are obtained in customary manner, for example by treatment with an acid or a suitable anion exchange reagent. Internal salts of compounds of formula I that contain a free acidic group and a free basic group, can be formed, for example, by neutralising salts, such as acid addition salts, to the isoelectric point, for example with weak bases, or by treatment with liquid ion exchangers.

Salts can be converted in customary manner into the free compounds; metal and ammonium salts can be converted into the free compounds, for example, by treatment with suitable acids, and acid addition salts, for example, by treatment with a suitable basic agent. The free compounds can also be obtained by means of anion or cation exchange chromatography.

The starting compounds used for the preparation of the compounds of the formula I are known or can be prepared by methods known in the art.

The compounds of the present invention are useful in compositions, combinations and methods for the treatment and prophylaxis of various diseases attributed to thrombin-mediated and thrombin-associated functions and processes. These include myocardial infarction, stroke, pulmonary embolism, deep vein thrombosis, disseminated intravascular coagulation, peripheral arterial occlusion, restenosis following arterial injury or invasive cardiological procedures, acute or chronic atherosclerosis, edema and inflammation, various cell regulatory processes (e.g. secretion, shape changes, proliferation), cancer and metastasis, and neurodegenerative diseases.

The thrombin inhibitors of the present invention may be formulated into pharmaceutically useful compositions, such as by mixing with a pharmaceutically acceptable carrier or diluent. These compositions may be used for treating or preventing thrombotic diseases in a patient.

According to an alternate embodiment of the present invention, the thrombin inhibitors may be employed in compositions for treating thrombotic disease, and for decreasing the dosage of a thrombolytic agent required to establish reperfusion or prevent reocclusion in a patient. Additionally, the thrombin inhibitors of this invention may be used in compositions for decreasing reperfusion time or increasing reocclusion time in a patient treated with a thrombolytic agent. These compositions may comprise a pharmaceutically effective amount of a thrombin inhibitor of the present invention and a pharmaceutically effective amount of a thrombolytic agent such as a plasminogen activator.

In these compositions, the thrombin inhibitor and the thrombolytic agent work in a complementary fashion to dissolve blood clots, resulting in decreased reperfusion times and increased reocclusion times in patients treated with them. The thrombolytic agent dissolves the clot, while the thrombin inhibitor prevents newly exposed, clot-entrapped or clot-bound thrombin from regenerating the clot. The use of the thrombin inhibitor in the compositions of this invention advantageously allows the administration of a thrombolytic reagent in dosages previously considered too low to result in thrombolytic effects if given alone. This avoids some of the undesirable side effects associated with the use of thrombolytic agents, such as bleeding complications.

Thrombolytic agents which may be employed in the combinations and compositions of the present invention are those known in the art. Such agents include tissue plasminogen activator purified from natural sources, recombinant tissue plasminogen activator, streptokinase, urokinase, prourokinase, anisolated streptokinase plasminogen activator complex (ASPAC), animal salivary gland plasminogen activators and known, biologically active derivatives of any of the above. The thrombin inhibitor and the thrombolytic agent may be in the same or in separate dosage forms which are administered separately, but concurrently or sequentially. In sequential administration, the thrombin inhibitor may be given to the patient at a time from 5 hours before to 5 hours after administration of the thrombolyic agent. Preferably, the thrombin inhibitor is administered to the patient at a time from 2 hours before to 2 hours after administration of the thrombolytic agent.

The compositions of the invention may be administered to a patient in various ways, e.g. parenterally or topically. The compositions will be formulated using adjuvants and diluents suitable for the desired method of administration. Thus the compositions may be administered intravenously as bolus or by continued infusion, intramuscularly—including paravertebrally and periarticularly—subcutaneously, intracutaneously, intra-articularly, intrasynovially, intrathecally, intra-lesionally, periostally or by nasal, or topical routes.

Parenteral compositions are preferably administered intravenously either in a bolus form or as a constant infusion. If the thrombin inhibitor is being used as an antiplatelet compound, constant infusion is preferred. If the thrombin inhibitor is being used as an anticoagulant, a subcutaneous or intravenous bolus injection is preferred. For parenteral administration, the thrombin inhibitor may be either suspended or dissolved in a sterile vehicle, optionally together with other components, and sterilizing before filling into a suitable vial or ampule and sealing. Preferably, adjuvants such as a local anesthetic, preservatives, stabilizers, solution promoters may also and/or buffers be dissolved in the vehicle. The composition may then be frozen and lyophilized to enhance stability. In the case of suspensions, a surfactant or wetting agent and/or other adjuvant as mentioned above may be included in the composition to facilitate uniform distribution of its components.

Compositions formulated for topical administration may, for example, be in aqueous jelly, oily suspension or emulsified ointment form.

Said compositions are prepared according to conventional mixing or lyophilising methods, respectively, and contain about 0.1 to 75%, in the case of lyophilisates up to 100%, of the active ingredient.

The dosage of active compound administered is dependent on the species of warm-blooded animal (mammal), the body weight, age and individual condition, and on the form of administration.

A preferred pharmaceutically effective dose of the thrombin inhibitor of this invention is from 0.01 mg/kg body weight of the patient to be treated to 5 mg/kg body weight, preferably from 0.1 to 0.5 mg/kg.

When a thrombolytic agent is also used a pharmaceutically effective dose of the thrombolytic agent may be between 10% and 80% of the conventional dosage range, i.e. the dosage used when that agent is employed in a monotherapy.

The thrombin inhibitors of the invention may also be used in compositions and methods for coating the surfaces of invasive devices, resulting in a lower risk of clot formation or platelet activation in patients receiving such devices. Surfaces that may be coated with the compositions of this invention include, for example, prostheses, artificial valves, vascular grafts, stents and catheters. Methods for coating these devices are known to those of skill in the art. These include chemical cross-linking or physical adsorption of the thrombin inhibitor-containing compositions on to the surfaces of the devices.

Compositions containing the thrombin inhibitors of this invention may also be used in the treatment of tumor metastases, as indicated by the inhibition of metastatic growth. Examples of metastatic tumors which may be treated by the thrombin inhibitors of this invention include carcinoma of the brain, carcinoma of the liver, carcinoma of the lung, osteocarcinoma and neoplastic plasma cell carcinoma.

Compositions containing the thrombin inhibitors of the invention may also be used to inhibit thrombin-induced endothelial cell activation, including the repression of platelet activation factor (PAF) synthesis by endothelial cells. The compositions have important applications in the treatment of diseases characterized by thrombin-induced inflammation and edema, which is though to be mediated be PAF. Such diseases include adult respiratory distress syndrome, septic shock, septicemia, reperfusion damage, and for treating or preventing in septicemia and other diseases.

The thrombin inhibitors of the invention or compositions comprising them, may also be used as anticoagulants for extracorporeal blood, for instance in such processes as dialysis procedures, blood filtration, or blood bypass during surgery as well as in blood products which are stored extracorporeally for eventual administration to a patient and blood collected from a patient to be used for various assays. Such products include whole blood, plasma, or any blood fraction in which inhibition of coagulation is desired.

The mount or concentration of thrombin inhibitor in these types of compositions is based on the volume of blood to be treated or, more preferably, its thrombin content, and may be from 0.01 mg/60 ml of extracorporeal blood to 5 mg/60 ml of extracorporeal blood.

The thrombin inhibitors of this invention may also be used to inhibit clot-bound thrombin, which is believed to contribute to clot accretion, and to prevent thrombins extension. This is particularly important because commonly used anti-thrombin agents, such as heparin and low molecular weight heparin, are ineffective against clot-bound thrombin.

BRIEF DESCRIPTION OF THE DRAWINGS

In the following experimental part an embodiment of the present invention is described with reference to the accompanying drawing.

Figure 1:
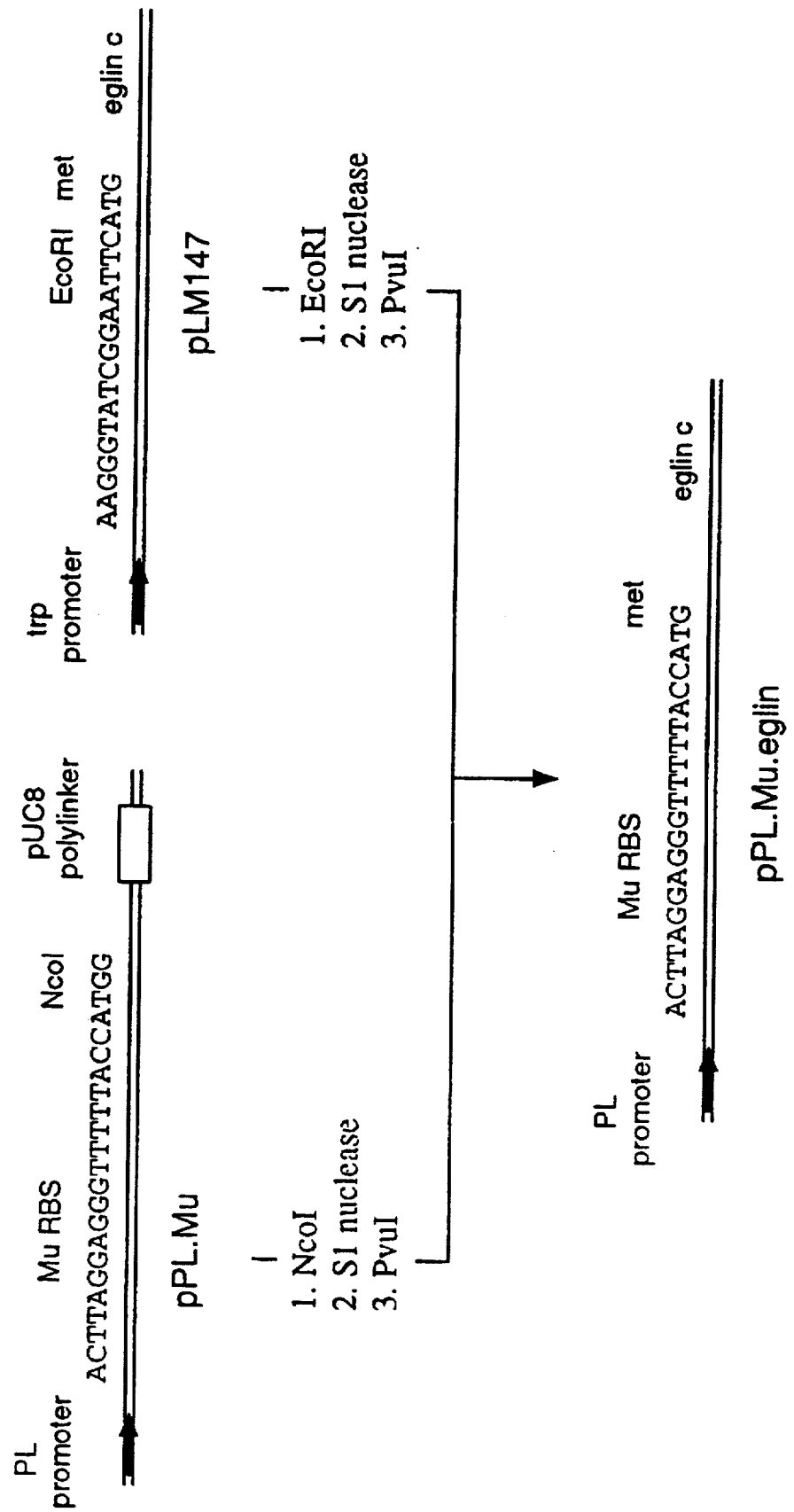
FIG. 1 is a schematic illustration of construction of pPL.Mu.eglin

The invention is illustrated by the following examples but should not be construed to be limited thereby.

Experimental Part

Abbreviations used:
Aca=6-Amino-hexanoic acid (Amino-caproic acid),
Apa=5-amino-pentanoic acid,
Gab=4-amino-butyric acid,
Apr=3-amino-propionic acid,
Aud=11-amino-undecanoic acid,
DICD=Diisopropylcarbodiimide,
DMA=Dimethylacetamide,
TFA=Trifluoro acetic acid
TFE=Trifluorethanol,
DCE=1,2-Dichloroethane,
DIPE=Diisopropylether,
DIEA=Diisopropylethylamine,
HOBt=1-Hydroxy-benzotriazole,
Pmc=2,2,5,7,8-pentamethylchroman-6-sulfonyl-,
TBTU=2-(1H-benzotriazol-1-yl)-1,1,3,3-tetramethyluronium tetrafluoroborate (R. Knorr et al., (1989) THL 30, 1927–1930),
DMF=Dimethylformamide,
THF=Tetrahydrofuran,
NMM=N-Methylmorpholin,
DMSO=Dimethylsulphoxide,
ACN=Acetonitrile.
NMP=N-methyl-pyrrolidone
PE=petrol-ether
TEAB-Buffer=1 m triethylammonium-bicarbonate
MALDI-MS=mass-assisted-laser-desorption-ionisation mass spectrometry Whenever occurring in the following examples, unless otherwise stated, the term "hirudin" denotes desulphatohirudin variant HV1.

EXAMPLE 1

$N^\alpha$-3-($\alpha,\alpha$-Dimethylbenzyl)benzenesulphonyl-(S)-arginyl chloride hydrochloride a) Orthanilic acid (1 kg) and α-methylstyrene (683g) are mixed with stirring in water (4.631) and heated at reflux for 8 hours. Further portions (2×148 g) of α-methylstyrene are added over 30 minute periods with refluxing for 6 hours. The mixture is filtered at 85° C. and the recovered solid product washed with boiling water and then with ethanol and dried in a vacuum oven. The product is stirred with ether (150ml), filtered off and dried. Recrystallisation from 50% aqueous ethanol affords 1-amino-4-(α,α-dimethylbenzyl)benzene-2-sulphonic acid, m.p. 263°–265° C.

b) 1-Amino-4-(α,α-dimethylbenzyl)benzene-2-sulphonic acid (582.7 g) is suspended in water (41) in a 201 reaction vessel, conc. HCl is added (400 ml) and the mixture is stirred and heated at 65° C. for 20 minutes. The suspension is cooled to 20° C. and conc. HCl (400 ml) is added, followed by a solution of NaNO$_2$ (138 g) in water (400 ml) dropwise, maintaining the temperature below 25° C. The resulting mixture is stirred at room temperature for a further 30 minutes. 50% Hypophosphorous acid (1.7 kg) is added dropwise over 30 minutes and the mixture is stirred at room temperature for 1 hour. The mixture is then warmed slowly until a temperature of 60° C. is reached and foaming has subsided to give a dark brown solution which is allowed to cool overnight and then filtered to remove a small amount of solid. The filtrate is evaporated to a volume of 41, neutralised by the gradual addition of sodium hydroxide pellets (950 g) to pH 10–11, water (31) is added and the solution warmed to 70° C. NaCl (800 g) is added and the product is allowed to crystallise. The solid is collected by filtration, washed with saturated brine and dried. After recrystallisation from 15% w/v NaCl(aq), the solid is stirred with ice water to remove salt, filtered and dried, stirred in acetone, filtered off and dried to give 3-(α,α-dimethylbenzyl) benzenesulphonic acid sodium salt. Further product is recovered from the washings.

c) 3-(α,α-Dimethylbenzyl)benzenesulphonic acid sodium salt (9.6 g) is dissolved in DMF (16 ml) and cooled to 10° C. Thionyl chloride (12ml) is added dropwise maintaining the temperature below 20° C. The mixture is allowed to warm to room temperature and stirred one hour. The solution is poured onto ice/water (100 ml) and the mixture is extracted with ether (3×8 ml). The combined extracts are dried (MgSO$_4$) and the solvent evaporated to give pale yellow waxy crystals which are dissolved in hexane (200 ml) and decolourised (charcoal). Evaporation produces white crystals of 3-(α,α-dimethylbenzyl)benzenesulphonyl chloride which are dried at room temperature under vacuum, m.p. 47.5°–49° C.

d) (S)-Arginine (12.6 g) and K$_2$CO$_3$ (12.03 g) are suspended in 50% water/dioxan (250 ml) with vigorous stirring and the reaction mixture is cooled to <5° C. 3-(α,α-

Dimethylbenzyl)benzenesulphonyl chloride (21.4g) is added in 6 portions over 30 minutes at <5° C. The mixture is stirred at 20° C. for 2 hours. A colourless solid precipitates. The dioxan is removed by evaporation and the aqueous residue is acidified with conc. HCl. The mixture is extracted with ethyl acetate (3×50ml) and the aqueous phase and all solid materials are combined and neutralised (4M NaOH). The suspension is stirred for 16 hours at 20° C. The solid precipitate is collected by filtration and stirred for 16 hours with a little water. The solid is collected by filtration and dried (NaOH pellets) to give $N^\alpha$-(3-($\alpha,\alpha$-dimethylbenzyl)benzenesulphonyl)-(S)-arginine, m.p. 122°–124° C. (Found: C, 53.49; H, 6.81; N, 11.92; S, 6.93. $C_{21}H_{28}N_4O_4S.2.3H_2O$ requires C, 53.22; H, 6.93; N, 11.82; S, 6.77%).

e) $N^\alpha$-(3-($\alpha,\alpha$-Dimethylbenzyl)benzenesulphonyl)-(S)-arginine (936 mg) is stirred with $SOCl_2$ (5 ml) for 2 hours at 20° C. Dry ether (40 ml) is added with vigorous stirring. The supernatant liquid is decanted from the white gum formed which is triturated with portions (2×40 ml) of dry ether. The gum is kept in vacuo (NaOH pellets) for 20 minutes to give a crisp white foam of $N^\alpha$-3-($\alpha,\alpha$-dimethylbenzyl)benzenesulphonyl-(S)-arginyl chloride.

EXAMPLE 2

1-($N^\alpha$-3-($\alpha,\alpha$-Dimethylbenzyl)benzenesulphonyl-(S)-arginyl)-4-(2-carboxyethyl)piperidine hydrochloride a) t-Butoxycarbonyl-Arg($NO_2$)-OH (11.7 g) is dissolved in DMF (60 ml) and N-methylmorpholine (4.04 ml) is added. The mixture is cooled to −10° C. and isobutyl chloroformate (4.8 ml) is added. The mixture is stirred at −10° C. for 10 minutes when a solution of 4-(2-carboxyethyl)piperidine methyl ester acetate salt (8.5 g) and N-methylmorpholine (4.04 ml) dissolved in DMF (60 ml) at −10° C. is added. The reaction mixture is stirred at −10° C. for 10 minutes and then allowed to come to room temperature over 30 minutes. The solvent is removed by evaporation and the residue dissolved in ethyl acetate (100 ml) and washed twice with 50 ml portions of cold 7% aqueous citric acid, brine, saturated aqueous $NaHCO_3$ (twice) and brine, dried ($Na_2SO_4$) and the solvent evaporated to give chromatographically-pure 1-((S)-$N^\alpha$-t-butyloxycarbonyl-$N^\omega$-nitroarginyl)-4-(2-carboxyethyl)piperidine methyl ester as a gum.

b) 1-((S)-$N^\alpha$-t-Butyloxycarbonyl-$N^\omega$-nitroarginyl)-4-(2-carboxyethyl)piperidine methyl ester (10 g) is dissolved in ethyl acetate (21 ml) and a solution of HCl in ethyl acetate (2N, 63.5 ml) is added. The mixture is stirred at room temperature for 2 hours and the solvent evaporated to yield a gum which is freed of excess of HCl by repeated addition of portions (100 ml) of ethyl acetate and evaporation of the solvent. The final chromatographically-pure gum is held in vacuo over NaOH pellets to afford 1-((S)-$N^\omega$-nitroarginyl)-4-(2-carboxyethyl)piperidine methyl ester hydrochloride.

c) 1-((S)-$N^\omega$-Nitroarginyl)-4-(2-carboxyethyl)piperidine methyl ester hydrochloride (1.97 g) is suspended in dichloromethane (12 ml) and N-methylmorpholine (1.16 ml) is added. The solution is cooled to 0° C. and 3-($\alpha,\alpha$-dimethylbenzyl)benzenesulphonyl chloride (1.4 g) is added in portions over 30 minutes at 0° C. After stirring for a further 30 minutes, dichloromethane (12 ml) is added and the solution is washed with brine (2×25 ml), dried ($Na_2SO_4$) and the solvent removed by evaporation. The product, 1-($N^\alpha$-3-($\alpha,\alpha$-dimethylbenzyl)-benzenesulphonyl-(S)-$N^\omega$-nitroarginyl)-4-(2-carboxyethyl)piperidine methyl ester, is isolated by flash chromatography on a column (150 g) of silica gel using $CHCl_3/CH_3OH$ (95:5 by vol.) as eluant.

d) 1-($N^\alpha$-3-($\alpha,\alpha$-Dimethylbenzyl)benzenesulphonyl-(S)-$N^\omega$-nitroarginyl)-4-(2-carboxyethyl)-piperidine methyl ester (1.7 g) is dissolved in a mixture of methanol (60 ml) and acetic acid (6 ml) and hydrogenated (1 atm.) in the presence of 10% Pd/C (0.5 g) at room temperature for 16 hours. The catalyst is removed by filtration and the solvent removed by evaporation. The residue is crystallised from methanol to give pure 1-($N^\alpha$-3-($\alpha,\alpha$-dimethylbenzyl)benzenesulphonyl-(S)-arginyl)-4-(2-carboxyethyl)-piperidine methyl ester acetate salt, m.p. 188°–190° C. Further pure material is isolated by flash chromatography using $CHCl_3/CH_3OH/CH_3COOH$ (6:1:1 by vol.) as eluant.

e) 1-($N^\alpha$-3-($\alpha,\alpha$-Dimethylbenzyl)benzenesulphonyl-(S)-arginyl)-4-(2-carboxyethyl)-piperidine methyl ester (1.07 g) is dissolved in methanol (10 ml) and dioxan (10 ml) and stirred for 3 hours at room temperature with aqueous 1N NaOH (6.8 ml). 1N $H_2SO_4$ (6.8 ml) is added and the solvents are removed by rotary evaporation and the residue dried by evaporation of several portions of ethanol from the residue. The product is extracted from the solid residue with hot ethanol and dried to yield product. This is dissolved in water (5 ml) and 1N HCl (0.77 ml) is added. The solid hydrochloride is collected by filtration, washed with water and dried to give 1-($N^\alpha$-3-($\alpha,\alpha$-dimethylbenzyl)benzenesulphonyl-(S)-arginyl)-4-(2-carboxyethyl)piperidine hydrochloride, m.p. 215° C. (Found: C, 57.3; H, 6.8; N, 11.3; S, 5.5; Cl, 5.5. $C_{29}H_{41}N_5O_5S.HCl$ requires C, 57.3; H, 7.0; N, 11.5; S, 5.3; Cl, 5.8%).

EXAMPLE 3

1-((S)-$N^\omega$-Nitroarginyl)-4-(6-carboxyhexyl)piperidine ethyl ester hydrochloride a) Thionyl chloride (1.03 ml) is added to 4-pyridinehexanol hydrochloride (2.42 g) and the mixture is stirred at 20° C. for 30 minutes. Excess saturated aqueous $NaHCO_3$ and $CHCl_3$ (20 ml) is added. The organic phase is washed with saturated $NaHCO_3$, brine and water, dried ($MgSO_4$) and the solvent evaporated to give crude material which is purified by flash chromatography on silica gel ($CH_3OH$:$CHCl_3$=1:49 by vol.) to give 4-(6-chlorohexyl)-pyridine as an oil.

b) NaCN (509 mg) in DMSO (4.25 ml) is added to 4-(6-chlorohexyl)pyridine (1.71 g) dissolved in DMSO (4.25 ml). The mixture is stirred at 60° C. for 3 hours, poured into water (100 ml) and extracted with chloroform (3×15 ml). The combined extracts are washed with water (2×20 ml), dried ($Na_2SO_4$) and the solvent evaporated to give 4-(6-cyanohexyl)-pyridine.

c) 4-(6-Cyanohexyl)pyridine (1.45 g) is stirred at 60°–70° C. for 72 hours with a mixture of ethanol (3.6 ml) and concentrated aqueous HCl (3.6 ml). The cooled reaction mixture is partitioned between water (20 ml) and chloroform (20 ml) and the separated organic phase dried ($Na_2SO_4$) and evaporated to yield 4-(6-carboxyhexyl)pyridine ethyl ester hydrochloride.

d) 4-(6-Carboxyhexyl)pyridine ethyl ester hydrochloride (1.17 g) is dissolved in $CH_3OH$ (22.5 ml) and acetic acid (2.5 ml) and hydrogenated (1 atm. $H_2$) in the presence of Adam's catalyst (100 mg) at 20° C. for 16 hours. The catalyst is removed by filtration and the solvents evaporated to give 4-(6-carboxyhexyl)piperidine ethyl ester hydrochloride which is kept in vacuo (NaOH pellets).

e) t-Butoxycarbonyl-Arg($NO_2$)-OH (31.9 g) is dissolved in DMF (465 ml) and N-methylmorpholine (NMM) (31.9 ml) is added. The mixture is cooled to −15° C. and isobutyl chloroformate (iBuOCOCl) (38 ml) is added. The reaction is stirred at −15° C. for 15 minutes. 4-(6-Carboxyhexyl) piperidine ethyl ester hydrochloride (97.4 g) is dissolved in DMF (465 ml) with NMM (31.9 ml) and the solution is cooled to −15° C. The two solutions are combined with stirring below −10° C. and stirring is continued for 30 minutes at −10° C. and then at 20° C. for 2 hours. The solvent is removed by evaporation and the residue is dissolved in ethyl acetate (300 ml) which is washed with portions (2×250 ml) of saturated aqueous $NaHCO_3$, brine, 7% aqueous citric acid and brine, dried ($Na_2SO_4$) and the solvent evaporated to yield 1-((S)-$N^\alpha$-t-butoxycarbonyl-$N^\omega$-nitroarginyl)-4-(6-carboxyhexyl)piperidine ethyl ester after flash chromatography on silica gel using ethyl acetate as solvent.

f) 1-((S)-$N^\alpha$-t-Butoxy-carbonyl-$N^\omega$-nitroarginyl)-4-(6-carboxyhexyl)piperidine ethyl ester (156 g) is dissolved in saturated HCl/$CH_3COOH$ (625 ml) and the reaction mixture is stirred at 20° C. for 2.5 hours. Evaporation of the solvent gives a chromatographically-pure residue of 1-((S)-$N^\omega$-nitroarginyl)-4-(6-carboxyhexyl)piperidine ethyl ester hydrochloride which is kept in vacuo (NaOH pellets) for direct use in following steps.

EXAMPLE 4

1-((S)-$N^\omega$-Nitroarginyl)-4-(4-carboxybutyl) piperidine ethyl ester hydrochloride In an analogous manner as described in example 3 but starting from 4-pyridine butanol hydrochloride instead of 6-pyridine hexanol hydrochloride, the title compound is prepared.

EXAMPLE 5

1-(3-Carboxypropyl)piperazine ethyl ester hydrochloride a) 1-Benzylpiperazine (3.7 g), ethyl 4-bromobutyrate (3.9 g) and triethylamine (2.93 ml) are stirred at 20° C. for 16 hours. The reaction mixture is partitioned between water (200 ml) and $CHCl_3$ (200 ml). The organic extract is dried ($MgSO_4$) and evaporated to give a yellow oil which is purified by elution from a pad of silica gel with ethyl acetate to give pure 1-benzyl-4-(3-carboxypropyl)piperazine ethyl ester as a colourless oil.

b) 1-Benzyl-4-(3-carboxypropyl)piperazine ethyl ester (4.7 g) is dissolved in ethanol (160 ml), 1N HCl (17.6 ml) is added and the mixture is hydrogenated (1 atm. $H_2$) in the presence of 10% Pd/C (0.47 g) at 20° C. until reaction is complete. The catalyst is removed by filtration and the filtrate evaporated to give 1-(3-carboxypropyl)piperazine ethyl ester hydrochloride as a gum containing residual solvent which is kept in vacuo (NaOH pellets).

EXAMPLE 6

1-(4-Carboxybutyl)piperazine ethyl ester hydrochloride a) Using the procedure described in Example 5a and ethyl 5-bromovalerate instead of ethyl 4-bromobutyrate there is obtained 1-benzyl-4-(4-carboxybutyl)piperazine ethyl ester as an oil after flash chromatography.

b) Using the procedure described in Example 5b and 1-benzyl-4-(4-carboxybutyl)piperazine ethyl ester instead of 1-benzyl-4-(3-carboxypropyl)piperazine ethyl ester there is obtained 1-(4-carboxybutyl)piperazine ethyl ester hydrochloride as an oil which crystallises on standing.

EXAMPLE 7

1-(5-Carboxypentyl)piperazine ethyl ester hydrochloride a) Using the procedure described in Example 5a and ethyl 6-bromohexanoate instead of ethyl 4-bromobutyrate there is obtained 1-benzyl-4-(5-carboxypentyl)piperazine ethyl ester as an oil.

b) Using the procedure described in Example 5b and 1-benzyl-4-(5-carboxypentyl)piperazine ethyl ester instead of 1-benzyl-4-(3-carboxypropyl)piperazine ethyl ester there is obtained 1-(5-carboxypentyl)piperazine ethyl ester hydrochloride as an oil which crystallises on standing.

EXAMPLE 8

1-(6-Carboxyhexyl)piperazine ethyl ester hydrochloride a) Using the procedure described in Example 5a and ethyl 7-bromoheptanoate instead of ethyl 4-bromobutyrate there is obtained 1-benzyl-4-(6-carboxyhexyl)piperazine ethyl ester as an oil.

b) Using the procedure described in Example 5b and 1-benzyl-4-(6-carboxyhexyl)piperazine ethyl ester instead of 1-benzyl-4-(3-carboxylpropyl)piperazine ethyl ester there is obtained 1-(6-carboxyhexyl)piperazine ethyl ester hydrochloride as an oil which crystallises on standing.

EXAMPLE 9

In a manner analogous to that described in Example 2 using 1-(3-carboxypropyl)piperazine ethyl ester hydrochloride, 1-(4-carboxybutyl)piperazine ethyl ester hydrochloride, 1-(5-carboxypentyl)piperazine ethyl ester hydrochloride and 1-(6-carboxyhexyl)piperazine ethyl ester hydrochloride, respectively, instead of 4-(2-carboxyethyl) piperidine methyl ester acetate salt as starting material the following compounds are prepared:

1-((S)-$N^\omega$-nitroarginyl)-4-(3-carboxypropyl)piperazine ethyl ester hydrochloride 1-((S)-$N^\omega$-nitroarginyl)-4-(4-carboxybutyl)piperazine ethyl ester hydrochloride 1-((S)-$N^\omega$-nitroarginyl)-4-(5-carboxypentyl)piperazine ethyl ester hydrochloride 1-((S)-$N^\omega$-nitroarginyl)-4-(6-carboxyhexyl)piperazine ethyl ester hydrochloride

EXAMPLE 10

In an analogous manner as described in example 2 the following compounds are prepared, starting from 3-(α,α-dimethylbenzyl)benzenesulphonyl chloride and 1-((S)-$N^\omega$-nitroarginyl)-4-(6-carboxyhexyl)piperidine ethyl ester hydrochloride, 1-((S)-$N^\omega$-Nitroarginyl)-4-(4-carboxybutyl) piperidine ethyl ester hydrochloride, 1-((S)-$N^\omega$-nitroarginyl)-4-(3-carboxypropyl)piperazine ethyl ester hydrochloride, 1-((S)-$N^\omega$-nitroarginyl)-4-(4-carboxybutyl)-piperazine ethyl ester hydrochloride, 1-((S)-$N^\omega$-nitroarginyl)-4-(5-carboxypentyl)piperazine ethyl ester hydrochloride, or 1-((S)-$N^\omega$-nitroarginyl)-4-(6-carboxyhexyl)piperazine ethyl ester hydrochloride:

1-($N^\alpha$-3-(α,α-dimethylbenzyl)benzenesulphonyl-(S)-arginyl)-4-(6-carboxyhexyl)piperidine hydrochloride, 1-($N^\alpha$-3-(α,α-dimethylbenzyl)benzenesulphonyl-(S)-arginyl)-4-(4-carboxybutyl)piperidine hydrochloride, 1-($N^\alpha$-3-(α,α-dimethylbenzyl)benzenesulphonyl-(S)-arginyl)-4-(3-carboxypropyl)piperazine hydrochloride, 1-($N^\alpha$-3-(α,α-dimethylbenzyl)benzenesulphonyl-(S)-arginyl)-4-(4-carboxybutyl)piperazine hydrochloride, 1-($N^\alpha$-3-(α,α-dimethylbenzyl)benzenesulphonyl-(S)-arginyl)-4-(5-carboxypentyl)piperazine hydrochloride, and 1-($N^\alpha$-3-(α,α-dimethylbenzyl)benzenesulphonyl-(S)-arginyl)-4-(6-carboxyhexyl)piperazine hydrochloride.

EXAMPLE 11

1-($N^\alpha$-(3-(α,α-Dimethylbenzyl)benzenesulphonyl)-(S)-arginyl)-piperidine-4-acetic acid a) To a stirred and cooled suspersion of (S)-$N^\alpha$-t-butoxycarbonyl-$N^\omega$-nitroarginine (3.1 g) in anhydrous tetrahydrofuran (THF) (50 ml) is added triethylamine (0.8 g) dropwise over 5 minutes at −20° C. and stirring is continued for a further 10 minutes. To the stirred mixture is then added isobutyl chloroformate (1.1 g) dropwise over 10 minutes at −20° C. and the mixture is stirred for a further 10 minutes. To the stirred mixture is then added 4-(ethoxycarbonylmethyl)piperidine (1.4 g) in THF (20 ml) dropwise over 10 minutes at −20° C. and then after stirring for a further 10 minutes at −20° the mixture is allowed to warm to room temperature with stirring for 1 hour. The reaction mixture is concentrated by evaporation and the residue is diluted with ethyl acetate (100 ml) and the mixture is washed with portions of water (3×15 ml), aqueous 5% $NaHCO_3$ (2×15 ml), aqueous 10% citric acid (2×15 ml), then water (2×15 ml) and dried ($MgSO_4$). Solvent is evaporated to give an oil which is chromatographed on silica gel using ethyl acetate as eluant to yield 1-((S)-$N^\alpha$-t-butoxycarbonyl-$N^\omega$-nitroarginyl)-4-(ethoxycarbonylmethyl)piperidine as a pale yellow oil, Rf (ethanol)=0.16.

b) To a stirred solution of 1-((S)-$N^\alpha$-t-butoxycarbonyl-$N^\omega$-nitroarginyl)-4-(ethoxycarbonylmethyl)piperidine (1.2 g) in dichloromethane (25 ml) cooled to 0° to 5° C. is slowly added trifluoroacetic acid (2.8 g) and the reaction mixture is allowed to warm to room temperature and is then stirred for 6 hours. Toluene (30 ml) is then added and the mixture is concentrated by evaporation and then co-evaporated with further toluene portions (2×30 ml) and the eventual residue is triturated with ether, collected by filtration, washed with ether and dried to constant weight in vacuo to give 1-((S)-$N^\omega$-nitroarginyl)-4-(ethoxycarbonylmethyl)-piperidine trifluoroacetate as a white solid, $R_f$(BuOH/$CH_3$COOH/$H_2O$ 3:2:1)=0.50.

c) The above 1-((S)-$N^\omega$-nitroarginyl)-4-(ethoxycarbonylmethyl)piperidine trifluoroacetate (2.1 g) is suspended in dry $CH_2Cl_2$ (50 ml) and stirred at 0° to 5° C. during the addition of triethylamine (1.3 g) to give a solution. To this solution is added dropwise at 0°–5° C. a solution of 3-(α,α-dimethylbenzyl)benzenesulphonyl chloride (1.2 g) in dry $CH_2Cl_2$ (5 ml) and the reaction mixture is then stirred at 20° C. for 3 hours. The reaction mixture is then diluted by addition of $CH_2Cl_2$(50 ml), washed with brine (3×150 ml) and the organic layer is dried ($MgSO_4$) and concentrated by evaporation to give a solid residue which is purified by chromatography on silica gel using ethylacetate/methanol (9:1) as eluant. Thus is obtained 1-($N^\alpha$-(3-(α,α-dimethylbenzyl)benzenesulphonyl)-(S)-$N^\omega$-nitroarginyl)-4-(ethoxycarbonylmethyl)piperidine as a pale yellow oil, $R_f$(EtOH)=0.21.

d) 1-($N^\alpha$-(3-(α,α-Dimethylbenzyl)benzenesulphonyl)-(S)-$N^\omega$-nitroarginyl)-4-(ethoxycarbonylmethyl)piperidine (300 mg) is dissolved in a mixture of $C_2H_5OH$ (150 ml) and $CH_3COOH$ (2 ml) and hydrogenated (50 atm. $H_2$) in the presence of 5% Pd/C (30 mg) for 5 hours at 35° C. After removal of the catalyst, the mixture is concentrated by evaporation to give an oily residue which is dissolved in ethyl acetate (20 ml) and washed with portions of saturated $Na_2CO_3$ (3×5 ml), saturated NaCl (3×5 ml), dried ($MgSO_4$) and evaporated to give a residue. The residue is dissolved in isopropanol (10 ml), stirred with charcoal for 2 hours, filtered and evaporated to give a solid which is triturated with ether, collected by filtration, washed with ether and dried in vacuo. Thus is obtained a white solid which is 1-($N^\alpha$-(3-(α,α-dimethylbenzyl)benzenesulphonyl)-(S)-arginyl)-4-(ethoxycarbonylmethyl)-piperidine, m.p. 144° C., $R_f$(BuOH/HOAc/$H_2O$ 3:1:1)=0.59. $^{13}$C NMR spectrum is consistent with the product.

e) To a suspension of 1-($N^\alpha$-(3-(α,α-dimethylbenzyl)benzenesulphonyl)-(S)-arginyl)-4-(ethoxycarbonylmethyl)piperidine (500 mg) in absolute ethanol (2.5 ml) is added aqueous 1M NaOH (1.7 ml) and the mixture is stirred for 24 hours at room temperature. The reaction mixture is then chromatographed on Amberlite resin CG120($H^+$) (25 ml). The resin column is eluted fast with aqueous 50% ethanol until neutral pH, then with ethanol/$H_2O$/$NH_3$ (sp.gr. 0.88) (5:4:1). The fractions containing the product are evaporated to give a residue which is co-evaporated (3 times) with ethanol, triturated with ether, collected by filtration, washed with ether and dried in vacuo. Thus is obtained 1-($N^\alpha$-(3-(α,α-dimethylbenzyl)benzenesulphonyl)-(S)-arginyl) piperidine-4-acetic acid, m.p. 188°–191° C., $R_f$(BuOH/HOAc/$H_2O$ 3:1:1) 0.58. $^{13}$C NMR spectrum is consistent with the product.

EXAMPLE 12

1-($N^\alpha$-3-(α,α-dimethylbenzyl)benzenesulphonyl-(S)-arginyl)-piperidine-acetic acid 4-(Ethoxycarbonylmethyl)-piperidine(357mg) and $Et_3N$ (0.28 ml) are dissolved in DMF (5 ml) and cooled in ice. $N^\alpha$-(3-(α,α-Dimethylbenzyl)benzenesulphonyl)-(S)-arginyl chloride hydrochloride (953 mg) dissolved in DMF (2 ml) is added dropwise during 10 minutes with stirring below 5° C. (pH >9). After stirring for a further 30 minutes, the mixture is filtered and the filtrate is evaporated to dryness and the residual oil is freed of DMF by co-evaporation of the residue with ethanol (2×5 ml). The resultant oil is dissolved in methanol (2 ml) and added dropwise to vigorously stirred Na-dried ether (25 ml). The supernatant liquid is decanted and the residual gum held in vacuo (conc. $H_2SO_4$) to give a crisp foam. The product is isolated from the foam by preparative HPLC (Zorbax C8) using $CH_3CN$/$H_2O$/$CF_3COOH$ (330:670:1 by vol.) to give crude product which is isolated by dissolution in a mixture of 1M $CH_3COOH$ (3 ml) and 1N HCl (2 ml) and passage through a column (40×3 cm) of Biogel-P2 resin which is eluted with aqueous 1M $CH_3COOH$. From this crude product there is obtained pure 1-($N^\alpha$- 3-(α,α-dimethylbenzyl)benzenesulphonyl-(S)-arginyl)-2-(4-ethoxycarbonylmethyl)piperidine hydrochloride.

The obtained ester is subjected to hydrolysis following the procedure described in Example 8e) to yield 1-($N^\alpha$-3-(α,α-dimethylbenzyl)benzenesulphonyl-(S)-arginyl)-piperidine-acetic acid. The product is identical with that obtained by the procedure described in Example 11.

EXAMPLE 13

The following compound is prepared in a similar manner to that described in example 11:

2-(1-(N$^\alpha$-(3-($\alpha,\alpha$-dimethylbenzyl)benzenesulphonyl)-(S)-arginyl)piperidine-4-yl)ethane sulphonic acid, m.p. 182°-4° C.

The values of elemental analysis (C, H, N, S) fit satisfactorily with the expected values.

EXAMPLE 14

3-(1-(N$^\alpha$-(3-($\alpha,\alpha$-dimethylbenzyl)benzenesulphonyl)-(S)-arginyl)-piperid-4-yl)-propionyl-(Gly)$_4$-Asn-hirudin(54-64) (BTI-1)

a) Protected BTI-1/resin

The construction of the peptidic part of BTI-1 is accomplished by Merrifield synthesis starting from Fmoc-Leu-p-benzyloxybenzyl ester-polystyrene resin (1% crosslinked, Novabiochem, Läufelfingen, Switzerland), in which the carboxy group of L-leucine, of which the amino group is protected by 9-fluorenyl-methoxycarbonyl (Fmoc), is esterified with 4-methoxybenzyl alcohol in which the carbon atom of the methoxy group is bonded to an aromatic ring of the polystyrene resin, 1% crosslinked with divinylbenzene, which simultaneously acts as a carrier. For this there is used a fully automatic peptide synthesis apparatus that is suitable for the alternate removal of the amino-protecting groups, in the present case the Fmoc group, and coupling of the Fmoc-amino acid derivatives without isolation of the peptide/resin intermediates obtainable at each step. Trifunctional amino acids are introduced as correspondingly protected derivatives: Fmoc-Ser(But) wherein the hydroxy group in the side chain of serine is protected by tert.butyl, Fmoc-Asp-OBut and Fmoc-Glu-OBut wherein the 3-carboxy group of aspartic acid and the 4-carboxy group of glutamic acid, respectively, are esterified with tert.butanol, Fmoc-Tyr(But) wherein the hydroxy group of tyrosine is protected by tert.butyl and Fmoc-Asn(Trt) wherein the 3-amide function of asparagine is protected by trityl (triphenylmethyl).

In a fast step, Fmoc-Tyr(But)-OH is coupled with the Leu/resin starting material, and then the other Fmoc amino acids are coupled in steps, in the following sequence, to the peptide/resin intermediate obtainable after each step: Fmoc-Glu(OBut)-OH, Fmoc-Glu(OBut)-OH, Fmoc-Pro-OH, Fmoc-Ile-OH, Fmoc-Glu(OBut)-OH, Fmoc-Glu(OBut)-OH, Fmoc-Phe-OH, Fmoc-Asp(OBut)-OH, Fmoc-Gly-OH, Fmoc-Asn(Trt)-OH, Fmoc-Gly-OH, Fmoc-Gly-OH, Fmoc-Gly-OH, Fmoc-Gly-OH (double couplings in the case of Gly). The individual steps are carried out in accordance with the following scheme, approximately 30 ml of the washing liquids being used in each case, with the individual operations, unless stated otherwise, being carried out at room temperature, and the reaction mixture being shaken regularly.

Starting from 3.2 g of the Fmoc-Leu/resin starting material (about 1.5 mMole), the following process steps, repeated for each step, are carried out:

single wash for 0.8 minutes with isopropanol;

pre-activation for first coupling: 4.5 mmol of the respective Fmoc-L-amino acid are dissolved in 12.4 ml of a 0.4 molar solution of HOBt in DMA and 4.95 ml of a 1 molar solution of DICD in DMA are added. The reaction mixture is maintained at room temperature, for about 40 minutes, and then used in that form. During this time the following washings and the removal of the Fmoc protecting group is already proceeding;

fifteen treatments of the resin starting material, each of 1 minute's duration, with a 20% solution of piperidine in DMA (removal of the Fmoc protecting group);

three washes, each of 0.4 minute's duration, with DMA degassed under reduced pressure;

single wash for 0.8 minutes with isopropanol;

five washes, each of 0.4 minute's duration, with DMA degassed under reduced pressure;

addition of the fast coupling reagent, which has been prepared in the meantime (see above). Pre-activation for second coupling: 4.5 mmol of the respective Fmoc-L-amino acid are dissolved in 12.4 ml of a 0.4 molar mixture of HOBt in DMA, and 4.95 ml of a 1 molar solution of DICD in DMA are added. The reaction mixture is maintained at room temperature, with stirring, for about 40 minutes, while the first coupling takes place;

removal of the coupling mixture after 40 minutes at room temperature from first coupling reaction;

addition of the second coupling reagent, which has been prepared in the meantime (see above). The coupling reaction is carried out for 30 minutes;

two washes for 0.4 minutes with DMA degassed under reduced pressure;

single treatment for 5 minutes with approximately 30 ml of a 1:1:8 mixture (v/v/v) of acetic anhydride, pyridine and DMA (for the acetylation of amino groups that are still free in the growing peptide chain);

four washes, each of 0.4 minute's duration, with DMA degassed under reduced pressure.

In this manner there is obtained the following Fmoc-peptide/resin intermediate:

Fmoc-Gly-Gly-Gly-Gly-Asn(Trt)-Gly-Asp(OBut)-Phe-Glu(OBut)-Glu(OBut)-Ile-Pro-Glu(OBut)-Glu(OBut)-Tyr(But)-Leu-resin, wherein "resin" denotes the carboxy group-esterifying polystyrene (1% crosslinked with divinylbenzene)-methoxy-4-phenylmethoxy radical.

After removal of the Fmoc protecting group at the N-terminal glycine residue (20% solution of piperidine in DMA, see above) of the peptide/resin intermediate (184 µMole, about 1.1 g) there is added a solution of 318 mg (523 µMole) of 1-(N$^\alpha$-3-($\alpha,\alpha$-dimethylbenzyl)benzenesulphonyl-(S)-arginyl)-4-(2-carboxyethyl)piperidine, 195 mg (607 µMole) TBTU and 104 mg (607 µMole) DIEA in 1.21 ml 0.5M HOBt in DMA. The mixture is kept at room temperature for 1 hour. The resulting protected BTI-1/resin 3-(1-(N$^\alpha$-(3-($\alpha,\alpha$-dimethylbenzyl)benzenesulphonyl)-(S)-arginyl)-piperid-4-yl)-propionyl-Gly-Gly-Gly-Gly-Asn(Trt)-Gly-Asp(OBut)-Phe-Glu(OBut)-Glu(OBut)-Ile-Pro-Glu(OBut)-Glu(OBut)-Tyr(But)-Leu-resin, is washed four times with isopropanol and dried under reduced pressure.

b) Removal of the polymeric carrier and the protecting groups

In order to remove the polymeric carrier, and the acid-labile protecting groups, 1.17 g of the peptide/resin compound (approximately 0.18 mmol) are shaken twice for 5 minutes at room temperature with 20 ml of a 98:2 mixture (v/v) of trifluoroacetic acid (95 %) and ethanedithiol and then filtered. The filtration residue is then washed three times with 20 ml each of DCE and 20 ml each of TFE. The combined filtrates and washing liquids are concentrated at room temperature under reduced pressure to a volume of approximately 20 ml, and the crude peptide is precipitated by the addition of about 120 ml of a 1:1 mixture (v/v) of DIPE and petroleum ether (low-boiling). The precipitate is isolated by filtration, washed with 50 ml of the precipitation mixture and dried under reduced pressure.

For purification, 50 mg aliquots of the crude peptide so obtained are dissolved in a mixture of 1.5 ml ACN/water (9:1 v/v) and 0.5 ml of acetic acid and subjected to high pressure liquid chromatography (HPLC) under the following conditions: the column, measuring 20×250 mm, Nucleosil 5C4(300E) manufactured by Macherey-Nagel, Düren, Federal Republic of Germany); 0.1% aqueous TFA is used as eluant (A) and a 0.1% solution of TFA in ACN is used as eluant (B). The linear gradient is 10% B→>50% B in 30 minutes, the throughput speed 15 ml/min and the detection in UV light 215 nm. The main fraction, with a retention time of approximately 14 minutes, is collected, concentrated under reduced pressure and lyophilised. After relyophilisation from acetic acid (95%) the title compound BTI-1 is obtained as a colourless solid.

HPLC: column Nucleosil 7C 18 (Macherey-Nagel, Düren, Federal Republic of Germany), dimension: 4.6×250 mm; eluant (A): 0.1% aqueous TFA, linear gradient 10% B→>90% B in 30 minutes, 1 ml/min, detection in UV light 215 nm. Retention time of the single peak: 19.7 min. FAB-MS (M$^+$–H): 2237.0 (calculated molecular weight: 2237.4).

EXAMPLE 15

In a manner analogous to that described in example 14 the following compound is prepared:

3-(1-(N$^\alpha$-(3-($\alpha,\alpha$-dimethylbenzyl)benzenesulphonyl)-(S)-arginyl)-piperid-4-yl)-propionyl-(Gly)$_3$-Asn-hirudin (54-64) (BTI-2), HPLC: retention time 18.1 min; FAB-MS (M$^+$–H): 2180.4 (calculated molecular weight: 2180.4);

The HPLC conditions are as described in example 14.

EXAMPLE 16

3-(1-(N$^\alpha$-(3-($\alpha,\alpha$-dimethylbenzyl)benzenesulphonyl) -(S)-arginyl)-piperid-4-yl)-propionyl-Gab-Aca-Asn-hirudin(54-64) (BTI-3)

The non-peptidic part of the title compound is assembled at the solid phase in a stepwise manner by using 3-($\alpha,\alpha$-dimethylbenzyl)benzenesulphonyl chloride, Fmoc-Arg (Pmc) (Pmc: 2,2,5,7,8-pentamethyl-chroman-6-sulphonyl, protecting group of the guanidino function of arginine) and Fmoc-carboxy-ethyl-piperidine as building blocks.

a) Preparation of Fmoc-4-(2-carboxyethyl)-piperidine 1.18 g (5.43 mMol) 4-(2-carboxyethyl)-piperidine-acetate are dissolved in 6.0 ml water and 1.50 ml (10.8 mMol) triethylamine. 2.75 g (8.15 mMol) fluorenyl-methoxy-carbonyl-N-hydroxy-succinimid ester (suspended in 6.0 ml acetonitrile) are added and the mixture is stirred at room temperature for 4 h. Twice, after 1½ and 3 h, 183 mg (1.09 mMol) fluorenyl-methoxy-carbonyl-N-hydroxy-succinimid ester is added. After addition of 5.5 ml 2N HCl, the mixture is dissolved in 200 ml ethylacetate and washed 6 times with 30 ml of water. After drying the organic phase with sodium sulfate and evaporation of the solvent in vacuo, the resulting oil is crystallized from ethylacetate/petrolether. Fp. 117°–119.5° C. (not corrected). The product is found to be homogeneous by tlc and the structure is confirmed by 1H-NMR.

b) Solid phase synthesis and attachment of non-peptidic part

The peptidic part is prepared as described for BTI-1 (cf. example 14). After having attached the peptidic linker part (Fmoc-Aca and Fmoc-Gab; Aca: 6-amino-caproic acid, Gab: 4-amino-butyric acid), Fmoc-carboxy-ethyl-piperidine and Fmoc-Arg(Pmc) using the standard protocol, the 3-($\alpha,\alpha$-dimethylbenzyl)benzenesulphonyl group is linked as follows:

24.1 mg (81.7 µMole) 3-($\alpha,\alpha$-dimethylbenzyl) benzenesulphonyl chloride and 14 µl (81 µMole) DIEA in 0.26 ml DMA/pyridine (1:1 v/v) are added to 160 mg Arg(Pmc)-(Carboxy-ethyl-piperidine)-Gaba-Aca-Asn-hirudin(54-64)-benzyloxybenzylester-resin (27 µMole) and reacted for 40 min at room temperature. The same amount of 3-($\alpha,\alpha$-dimethylbenzyl)benzenesulphonyl chloride is then added and reacted for an additional 50 min. The resin is washed with DMA and isopropanol as described. Cleavage from the resin is done as described for BTI-1 (cf. example 14). For removing the side-chain protecting groups (Pmc!) an additional treatment with TFA(95%)/ethandithiol (4:1 v/v) for 2 hours at room temperature is required. Isolation and purifications are performed as described for BTI-1.

BTI-3 is characterized as follows:

HPLC: retention time 20.5 min (conditions as described in example 14); FAB-MS (M$^+$–H): 2206.8 (calculated molecular weight: 2207.5).

EXAMPLE 17

The following compounds are prepared in the same manner as described in example 16:

3-(1-(N$^\alpha$-(3-($\alpha,\alpha$-dimethylbenzyl)benzenesulphonyl)-(S)-arginyl)-piperid-4-yl)-propionyl-Aud-Asn-hirudin(54-64) (Aud: 11-amino-undecanoic acid) (BTI-4), 3-(1-(N$^\alpha$-(3-($\alpha,\alpha$-dimethylbenzyl)benzenesulphonyl)-(S)-arginyl)-piperid-4-yl)-propionyl-Gab-(Gly)$_2$-Asn-hirudin (54-64) (BTI-5), 3-(1-(N$^\alpha$-(3-($\alpha,\alpha$-dimethylbenzyl)benzenesulphonyl)-(S)-arginyl)-piperid-4-yl)-propionyl-Apr-(Gly)$_2$-Asn-hirudin (54-64) (Apr: 3-amino-propionic acid) (BTI-6), 3-(1-(N$^\alpha$-(3-($\alpha,\alpha$-dimethylbenzyl)benzenesulphonyl)-(S)-arginyl)-piperid-4-yl)-propionyl-Gly-Glu-(Gly)$_2$-Asn-hirudin(54-64) (BTI-7), 3-(1-(N$^\alpha$-(3-($\alpha,\alpha$-dimethylbenzyl)benzenesulphonyl)-(S)-arginyl)-piperid-4-yl)-propionyl-Gly-Lys-(Gly)$_2$-Asn-hirudin(54-64) (BTI-8), 3-(1-(N$^\alpha$-(3-($\alpha,\alpha$-dimethylbenzyl)benzenesulphonyl)-(S)-arginyl)-piperid-4-yl)-propionyl-Gly-Phe-(Gly)$_2$-Asn-hirudin(54-64) (BTI-9), The HPLC retention times (rt, expressed in minutes, min, conditions see example 14) and the molecular weights (calculated molecular weights) as determined by FAB-MS (FAB) and laser desorption MS (LD), respectively, of the compounds are as follows:

| inhibitor | rt(min) | MS |
|---|---|---|
| BTI-4 | 22.4 | 2191.6 (2192.6) LD |
| BTI-5 | 20.0 | 2207.5 (2208.4) LD |
| BTI-6 | 20.2 | 2193.0 (2194.4) LD |
| BTI-7 | 19.8 | 2309.2 (2309.5) LD |
| BTI-8 | 19.0 | 2307.7 (2308.6) LD |
| BTI-9 | 21.1 | 2327.2 (2327.6) LD |

EXAMPLE 18

In a manner analogous to that in the preceding examples the following compounds are prepared:

3-(1-(N$^\alpha$-(3-($\alpha,\alpha$-dimethylbenzyl)benzenesulphonyl)-(S)-arginyl)-piperid-4-yl)-propionyl-Apr-Apa-Asn-hirudin (54-64), 3-(1-(N$^\alpha$-(3-($\alpha,\alpha$-dimethylbenzyl)benzenesulphonyl)-(S)-arginyl)-piperid-4-yl)-propionyl-(Gly)$_4$-Asn-[homoPhe$^{56}$]hirudin(54-64), 7-(1-(N$^\alpha$-(3-($\alpha,\alpha$-dimethylbenzyl)benzenesulphonyl)-(S)-arginyl)-piperid-4-yl)-heptanoyl-(Gly)$_2$-Asn-hirudin(54-64), 5-(1-(N$^\alpha$-(3-($\alpha,\alpha$-dimethylbenzyl)benzenesulphonyl)-(S)-arginyl)-piperid-4-yl)-pentanoyl-(Gly)$_3$-Asn-hirudin(54-64), 4-(1-(N$^\alpha$-(3-($\alpha,\alpha$-dimethylbenzyl)benzenesulphonyl)-(S)-arginyl)-piperazin-4-yl)-butanoyl-(Gly)$_3$-Asn-hirudin (54-64), 5-(1-(N$^\alpha$-(3-($\alpha,\alpha$-dimethylbenzyl)benzenesulphonyl)-(S)-arginyl)-piperazin-4-yl)-pentanoyl-(Gly)$_3$-Asn-hirudin (54-64), 6-(1-(N$^\alpha$-(3-($\alpha,\alpha$-dimethylbenzyl)benzenesulphonyl)-(S)-arginyl)-piperazin-4-yl)-hexanoyl-(Gly)$_3$-Asn-hirudin (54-64), 7-(1-(N$^\alpha$-(3-($\alpha,\alpha$-dimethylbenzyl)benzenesulphonyl)-(S)-arginyl)-piperazin-4-yl)-heptanoyl-(Gly)$_2$-Asn-hirudin (54-64), 2-(1-(N$^\alpha$-(3-($\alpha,\alpha$-Dimethylbenzyl)benzenesulphonyl(S)-arginyl)-piperid-4-yl)-acetyl-(Gly)$_4$-Asn-hirudin(54-64), 2-(1-(N$^\alpha$-(3-($\alpha,\alpha$-dimethylbenzyl)benzenesulphonyl)-(S)-arginyl)-piperid-4-yl)-ethane sulphonyl-(Gly)$_4$-Asn-hirudin(54-64).

EXAMPLE 19

Pharmaceutical Composition for Parenteral Administration

A solution containing a BTI compound according to any one of the examples 13–16 is dialysed against a 0.9% NaCl solution. The concentration of the solution is then adjusted by diluting with the same NaCl solution to 0.2 to 2.0 mg/ml. The resulting solutions are sterilized by ultrafiltration (membranes with 0.22 μm pores).

The sterilized solutions can be used directly, for example for intravenous administration.

EXAMPLE 20

Construction of Expression Vector for Expression of Eglin c behind the λP$_L$ promoter All DNA manipulations are—unless otherwise noted—carried out according to standard protocols (e.g. Maniatis, T. et al.: Molecular cloning: a laboratory manual. Cold Spring Harbor Laboratory, Cold Spring Harbor, N.Y. (1982).

Plasmid pPL.Mu is plasmid pPLmuSMCori (Buell et al., Nucleic Acids Res. 13, 1923–1938 (1985)) carrying between the single NcoI and HindIII sites the pUC8 poly-cloning site (Vieira and Messing, Gene, 19, 259–268 (1982)). Plasmid pML147 contains the genes for eglin c behind the tryptophan promoter (Rink et al., Nucleic Acids Res., 12, 6369–6387 (1984)). Plasmid pPL.Mu and pLM147 are linearized with the restriction endonuclease NcoI and EcoRI, respectively. The 5' protruding ends of these DNA's are removed by nuclease S1 digestion (100 mM NaCl; 50 mM CH$_3$COONa; 0.1 mM ZnCl$_2$; acetic acid to pH4.5, 30 min. at more temperature). The plasmids are then separately cut at the PvuI site in the gene coding for β-lactamase and the DNA fragment from pPL.Mu containing the λ promoter and the fragment of pLM147 containing the eglin c gene are isolated form agarose gels and ligated resulting in plasmid pPL.Mu.eglin (FIG. 1 ).

EXAMPLE 21

Heat Induction

E. coli strain SG936 (ATCC 39624) is freshly transformed with plasmids pcI857 (Buell et at., Nucleic Acids Res. 13, 1923–1938 (1985); Remaut et al., Gene 22, 103–113 (1983)) and pPL.Mu.eglin and plated on LB plates containing ampicillin and kanamycin. A 50 ml overnight culture grown at 30° C. in LB containing 40 mg/l of ampicillin and kanamycin is added to a 1000 ml erlenmeyer flask containing 200 ml of the same medium at room temperature. The culture is heated to 42° C. while shaking in a 65° C. water bath then transferred to a 42° C. water bath shaker. Cells are harvested by centrifugation after 5 h incubation. The cell paste is frozen and kept at –76° C.

EXAMPLE 22

Construction of Expression Vector for Expression of Eglin c-(Gly)$_2$Thr-Tys-(Gly)$_4$-Asn-hirudin(54-64) behind the λ P$_L$ promoter Two synthetic oligonucleotides which partially hybridize to each other (SEQ ID NO:7 and SEQ ID NO:8)

| TATAGTTAAC | CATGTTCCGC | ATGTTGGTGG | TGGCACTAAG | GGTGGCGGTG | GCAAC | 55 |
|---|---|---|---|---|---|---|
| and | | | | | | |
| TATAGGATCC | TAGAGGTACT | CTTCAGGGAT | CTCTTCGAAA | TCACCGTTGC | CACCGCCACC | 60 |
| C | | | | | | 61 | are used in a polymerase chain reaction (PCR). The double stranded DNA fragment obtained in this reaction codes for the 8 C-terminal aminoacids of eglin followed by (Gly)$_2$-Thr-Lys-(Gly)$_4$-Asn-hirudin(54-64) followed by a translation stop codon and are flanked by a HpaI and a BamHI restriction site. This DNA fragment is isolated from an agarose gel, cut with HpaI and BamHI and ligated into the HpaI and BamHI cut pPL.Mu.eglin vector resulting in plasmid pPL.Mu.eglin-hir, which is now used for expression of the fusion protein eglin c-(Gly)$_2$-Thr-Lys-(Gly)$_4$-Asn-hirudin(54-64) (SEQ ID NO:9).

EXAMPLE 23

Isolation of the Fusion Protein Eglin-(Gly)$_2$-Thr-Lys-(Gly)$_4$-Asn-hirudin(54-64)

3.1 g cells from 1.6 l fermentation-suspension are suspended in 16 ml acetic acid/water (1:9 v/v) and sonified 2 times for 45 sec. (pulsed mode). The supernatant is dried under reduced pressure after centrifugation at 4° C. The raw-product (118 mg) contains 14.8 mg pure fusion protein (calculated from a comparison via HPLC with purified material). The fusion protein can be purified by HPLC using nucleosil 10C18®, eluent 10%→90% acetonitrile (0,1% TFA), in 30 min., 15 ml/min and detection at 215 nm (purity >98%, MALDI-MS: correct mass).

EXAMPLE 24

Trypsine-cleavage of Eglin-(Gly)$_2$-Thr-Lys-(Gly)$_4$-Asn-hirudin(56-64)

9.5 mg of the raw product according to example 23 (1.1 mg eglin-(Gly)$_2$-Thr-Lys-(Gly)$_4$-Asn-hirudin(56-64)) are dissolved in 5 ml water and 150 µl TEAB-buffer. At 37° C. 30 µg trypsine (Boehringer, sequencing grade) are added and after 2.5 h further 20 µg trypsine are added. After a total incubation time of 4 h the mixture is concentrated at 25° C. to 1 ml under reduced pressure. The purification is carried out on a mono-Q column:

buffer A: 50 mM TEAA, 0.01M NaCl
buffer B: 50 mM TEAA, 1M NaCl
gradient: 0% B→40% B, 26 min.
detection at 260 nm.

The obtained (Gly)$_4$-Asn-hirudin(54-64) has a purity of >98% (MALDI-MS: correct mass)

EXAMPLE 25

Coupling of unprotected 1-(N$^\alpha$-3-($\alpha,\alpha$-dimethylbenzyl)benzenesulphonyl)-(S)-arginyl)-4-(2-carboxyethyl)piperidine to (Gly)$_4$-Asn-hirudin (56-64)

8.6 mg (15 µmol) 1-(N$^\alpha$-3-($\alpha,\alpha$-dimethylbenzyl)benzenesulphonyl-(S)-arginyl)-4-(2-carboxyethyl)piperidine are dissolved in 100 µl NMP containing 15 µmol DIEA and 4.8 mg (15 µmol) TBTU are added. After 5 min. at room temperature 16.8 mg of (Gly)$_4$-Asn-hirudin(54-64) are added and diluted with 40 µl NMP. 2.57 µl (15 µmol) DIEA are added after 5 min. After 45 min. the reaction mixture is dropped into 1 ml of DIPE/PE (1:1 v/v). The obtained oil is collected via centrifugation, washed once with 0.5 ml DIPE/PE (1:1 v/v) and 3 times with 200 µl water. The resultant is dried under reduced pressure using P$_2$O$_5$ (15.9 mg). The purification is carried out using a nucleosil 7C$_{18®}$ column (100 Å) 20×250 min.

gradient: 10%→90% acetonitrile (0.1% TFA), 60 min., 18 ml/min. detection at 215 nm.

The obtained 1-(N$^\alpha$-3-($\alpha,\alpha$-dimethylbenzyl)benzenesulphonyl-(S)-arginyl)-4-(2-carboxyethyl)piperidine-(Gly)$_4$-Asn-hirudin(54-64) has a purity of >98% (MALDI-MS)

EXAMPLE 26

Synthesis of Pmc Protected 1-(N$^\alpha$-3-($\alpha,\alpha$-dimethylbenzyl)benzenesulphonyl-(S)-arginyl)-4-(2-carboxyethyl)piperidine a) Coupling of the first amino acid to the resin 1.32 g (3.48 mol) Fmoc-4-(2-carboxyethyl)-piperidine (example 16a) are dissolved in 1.1 ml DMF and 14 ml 1,2-dichloroethane, 2.00 g (1.16 mmol hydroxy-function) hydroxy-trialkoxy-benzhydrylic-polystyrene (Novabiochem) are added and cooled to 0°–5° C. Over a period of 5 min. 766 mg (3.71 mmol) dicyclohexylcarbo-diimide dissolved in 1.4 ml dichloroethane and finally 56.7 mg (0.46 mmol) p-dimethylamino-pyridine are added. After 20 min. 117 mg (1.16 mmol) N-methyl-morpholine are added and the reaction mixture is kept at room temperature for 15 h. Than, the resin is washed extensively with isopropanole and dried under reduced pressure.

b) Construction of resin bound Pmc Protected 1-(N$^\alpha$-3-($\alpha,\alpha$-dimethylbenzyl)benzenesulphonyl-(S)-arginyl)-4-(2-carboxyethyl)piperidine To 1.7 g of the modified resin the following process is applied in a automatic peptide synthesizer: (All washing is carried out using 10 ml washing agent and reactant each)

single wash for 0.8 minutes with isopropanole;

pre-activation for first coupling: 1.59 g (2.4 mmol) of Fmoc-Arg(Pmc)-OH are dissolved in 5.28 ml (2.64 mmol) of a 0.5 molar solution of HOBt in DMA and 1.32 ml (2.64 mmol) of a 2 molar solution of DCCI in DMA are added. The reaction mixture is maintained at room temperature, for about 40 minutes, and then used in that form. During this time the following washings and the removal of the Fmoc protecting group is already proceeding;

seventeen treatments of the resin starting material, each of 1 minute's duration, with a 20% solution of piperidine in DMA (removal of the Fmoc protecting group);

three washes, each of 0.4 minute's duration, with DMA degassed under reduced pressure;

single wash for 0.8 minutes with isopropanol;

five washes, each of 0.4 minute's duration, with DMA degassed under reduced pressure;

addition of the coupling reagent, which has been prepared in the meantime (see above) and addition of 452 µl (1.64 mmol) DIEA.

removal of the coupling mixture after 60 minutes at room temperature from coupling reaction;

two washes for 0.4 minutes with DMA degassed under reduced pressure;

single treatment for 5 minutes with approximately 30 ml of a 1:1:8 mixture (v/v/v) of acetic anhydride, pyridine and DMA (for the acetylation of amino groups that are still free in the growing peptide chain);

four washes, each of 0.4 minute's duration, with DMA degassed under reduced pressure.

This process is repeated without the acetylation step:

Instead of the Fmoc-Arg(Pmc)-OH solution, 429 mg (1.45 mmol) phenyl-cumyl-sulfonylchloride (PCSCl) dissolved in 4.6 ml DMA together with 249 µl (1.45 mmol) DIEA are added to the resin. After 65 min. at room temperature, the liquid is removed. A second coupling is carried out using 268 mg (0.97 mmol) PCSCl dissolved in 3 ml DMA together with 166 µl (0.97 mmol) DIEA for 85 min. Finally the resin is washed five times with isopropanol and dried under high vacuum.

c) Removal of the polymeric carrier

In order to remove the polymeric carrier 1.0 g of the peptide/resin compound (approximately 0.24 mmol) are shaken for 1 h at room temperature with 10 ml of a 1:9 mixture (v/v) of acetic acid and DCE and then filtered. The filtration residue is then washed three times with 7 ml each of DCE and 7 ml each of TFE. The combined filtrates are concentrated under reduced pressure dissolved in 15 ml tert.butanol, dried under reduced pressure and characterized with MALDI-MS.

EXAMPLE 27

Coupling of Pmc Protected 1-($N^\alpha$-3-($\alpha,\alpha$-dimethylbenzyl)benzenesulphonyl-(S)-arginyl)-4-(2-carboxyethyl)piperidine to $(Gly)_4$-Asn-hirudin(56-64)

The coupling is carried out using 12.6 mg (15 μmol) Pmc-1-($N^\alpha$-3-($\alpha,\alpha$-dimethylbenzyl)benzenesulphonyl-(S)-arginyl)-4-(2-carboxyethyl)piperidine as described in example 25. The raw product is characterized with MALDI-MS.

EXAMPLE 28

Removal of the Pmc-group 0.5 mg raw product obtained from example 27 are kept for 2 h in 20 μl TFA (95%)/ethanedithiole (95:5 v/v) at room temperature. The reaction mixture is than added to 100 μl DIPE/PE (1:1 v/v). The colorless precipitate is cooled to 0°–5° C. and centrifuged. After washing 3 times with DIPF/PE (1:1 v/v) the white powder is dried under reduced pressure and identified with HPLC.

---

We claim:

1. A compound of the formula I

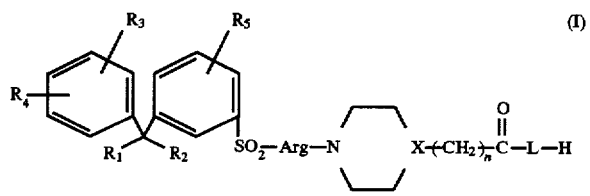

(I)

in which $R_1$ and $R_2$ are each $C_1$–$C_4$ alkyl, $R_3$, $R_4$ and $R_5$ are each hydrogen; Arg is arginine, X is selected from the group consisting of methine CH or nitrogen, n is an integer from 0 to 7; L is a peptide linker comprising 3 to 6 amino acids selected from the group consisting of a $C_2$–$C_{12}$-ω-amino carboxylic acid, alanine, serine, threonine, glutamine, asparagine, phenylglycine or phenylalanine, and H is the carboxy terminal end of hirudin starting with amino acid 55 and ending at the ultimate or penultimate amino acid of hirudin, a desulphated variant of such a hirudin comprising a tyrosine sulphate residue, a variant of such a hirudin in which the tyrosine sulphate residue is replaced by a tyrosine phosphate residue, or a derivative thereof in which 1-3 amino acids are replaced by other amino acids, which derivatives retain the binding affinity to thrombin, wherein the backbone chain (II) defined by the formula

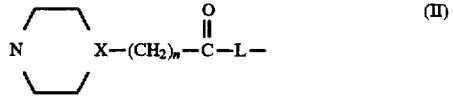

(II)

comprises about 18 to about 28, in particular about 22 to about 26, atoms and pharmaceutically acceptable salts thereof.

2. A compound of the formula (I) according to claim 1 in which $R^1$ and $R^2$ represent each methyl, $R^3$, $R^4$ and $R^5$ are each hydrogen; Arg is arginine; X is methine CH; n is 2; L is a peptide linker comprising 3 to 6 amino acids selected from the group consisting of a $C_2$–$C_{12}$-ω-amino carboxylic acid and asparagine; and H is the carboxy terminal end of hirudin variant HV1 starting with amino acid 55 and ending at the ultimate or penultimate amino acid of hirudin HV1 or a desulphated variant thereof; wherein the backbone chain (II) defined by the formula

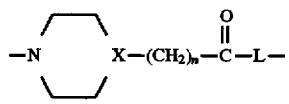

comprises about 22 to about 26 atoms; and pharmaceutically acceptable salts thereof.

3. A compound of the formula (I) according to claim 1 in which $R^1$ and $R^2$ each represent methyl, $R^3$, $R^4$ and $R^5$ are each hydrogen; Arg is arginine; X is methine CH; n is 2; L is a peptide linker comprising 3 to 6 amino acids selected from the group consisting of 6-amino-caproic acid, 4-amino-butyric acid, glycine and asparagine; and H is the carboxy terminal end of desulphatohirudin variant HV1 starting with amino acid 55 and ending at the penultimate amino acid of hirudin HV1 wherein the backbone chain (II) defined by the formula

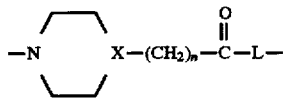

comprises 22 to 26 atoms; and pharmaceutically acceptable salts thereof.

4. A compound of the formula (I) according to claim 1 in which H is selected from the group consisting of Asp Phe Glu Glu Ile Pro Glu Glu Z Leu Gln (III, SEQ ID NO:1), Asp Phe Glu Pro Ile Pro Glu Asp Ala Z Asp Glu (IV, SEQ ID NO:2), Asp Phe Asp Pro Ile Pro Glu Glu Z Leu Ser (V, SEQ ID NO:3), and Asp Phe Glu Glu Phe Ser Leu Asp Asp Ile Glu Gln (VI, SEQ ID NO:4), wherein Z is Tyr, Tyr(SO₃H) or Tyr(PO₃H₂), in the latter two cases the hydroxy group of tyrosine being esterified with sulphuric acid and phosphoric acid, respectively, and in which the ultimate amino acid may be absent.

5. A compound of the formula (I) according to claim 1 in which H is Asp Phe Glu Glu Ile Pro Glu Glu Tyr Leu, (SEQ ID NO:11).

6. A compound of the formula (I) according to claim 1 in which the radical L-H is Gly Gly Gly Gly Asn Gly Gly Asp Phe Gln Glu Ile Pro Glu Glu Tyr Leu (IIIa, SEQ ID NO:5).

7. A compound of the formula (I) according to claim 1 in which the radical L-H is Gab Aca Ash Gly Asp Phe Glu Glu Ile Pro Glu Glu Tyr Leu (IVa, SEQ ID NO:6); wherein Gab designates 4-amino-butyric acid and Aca designates 6-amino-caproic acid.

8. 3-(1-(N$^\alpha$-(3-(α,α-dimethylbenzyl)benzenesulphonyl)-(S)-arginyl)-piperid-4-yl)-propionyl-Gab-Aca-Asn-hirudin (54-64) according to claim 1.

9. 3-(1-(N$^\alpha$-(3-(α,α-dimethylbenzyl)benzenesulphonyl)-(S)-arginyl)-piperid-4-yl)-propionyl-(Gly)₄-Asn-hirudin HV1(54-64) according to claim 1.

10. 3-(1-(N$^\alpha$-(3-(α,α-dimethylbenzyl)benzenesulphonyl)-(S)-arginyl)-piperid-4-yl)-propionyl-(Gly)₃-Asn-hirudin HV1(54-64) according to claim 1.

11. A pharmaceutical composition comprising a compound of the formula (I) or a pharmaceutically acceptable salt thereof according to claim 1.

12. A compound of the formula (I) according to claim 1 or a pharmaceutically acceptable salt thereof for use in a method for the prophylactic or therapeutic treatment of the human or animal body.

13. A method for the treatment and prophylaxis of diseases attributed to thrombin-mediated and thrombin-associated functions in a mammal which comprises administering to said mammal a compound of the formula (I) according to claim 1 or a pharmaceutically acceptable salt thereof.

14. A method of inhibiting thrombin in blood which comprises adding to the blood an effective amount of a compound of the formula (I) according to claim 1 or a pharmaceutically acceptable salt thereof.

15. Process for the production of a compound of the formula I according to claim 1 comprising reacting an amide bond forming first fragment of a compound of formula I with a second amide bond forming fragment of a compound of formula I, said first fragment and said second fragment being complementary to one another such that an amide bond is formed between said first and second fragments to result in said compound of formula I, one of said first and second fragments containing a reactive free carboxy group and sulphoxy group, respectively, or a reactive carboxylic acid or sulphonic acid derivative thereof, and the other of said first and second fragments containing a free amino group or a reactive derivative thereof, wherein free functional groups in the mentioned fragments, with the exception of the two groups participating in the reaction, are, if necessary, in protected form, and removing protecting groups which may be present, and, if desired, converting a salt obtainable in accordance with the process into the free compound and/or converting a free compound obtainable in accordance with the process into a salt.

16. A process for the production of a compound of the formula I according to claim 1 comprising a) constructing an expression cassette for a fusion protein comprising the carboxy terminal end of hirudin and optionally a peptide linker, b) expressing the fusion protein in a suitable host, c) isolating the carboxy terminal part of hirudin (H) optionally including the peptide linker (L) from the fusion protein, d) linking of the N-terminus of the carboxy terminal part of hirudin (H) optionally including the peptide linker (L) to the radical of the formula (XIII)

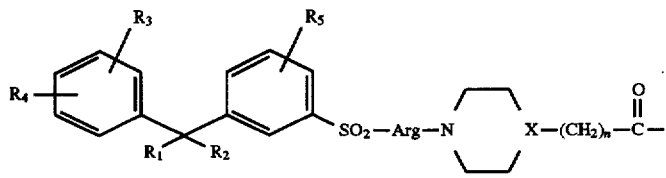

wherein residues R₁-R₅ and n have the meanings as defined in claim 1; or linking of the N-terminus of the hirudin fragment (H) to the peptide linker (L) and subsequently to the radical of the formula (XIII); or linking of the peptide linker (L) to the radical of the formula (XIII) and subsequently to the N-terminus of the hirudin fragment (H).

17. A compound obtained by the process according to claim 15.

18. A compound obtainable in accordance with the process according to claim 16.

* * * * *